United States Patent
Hayashi et al.

(10) Patent No.: US 10,858,589 B2
(45) Date of Patent: Dec. 8, 2020

(54) POLYMERIZABLE LIQUID CRYSTAL COMPOUND, POLYMERIZABLE COMPOSITION, AND FILM

(71) Applicant: FUJIFILM Corporation, Tokyo (JP)

(72) Inventors: Daisuke Hayashi, Ashigarakami-gun (JP); Hiroshi Inada, Ashigarakami-gun (JP); Shunya Katoh, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 213 days.

(21) Appl. No.: 15/898,295

(22) Filed: Feb. 16, 2018

(65) Prior Publication Data

US 2018/0171232 A1 Jun. 21, 2018

Related U.S. Application Data

(63) Continuation of application No. PCT/JP2016/077200, filed on Sep. 15, 2016.

(30) Foreign Application Priority Data

Sep. 18, 2015 (JP) ................. 2015-184756

(51) Int. Cl.

| | | |
|---|---|---|
| C09K 19/38 | (2006.01) | |
| C07D 241/04 | (2006.01) | |
| C07D 295/205 | (2006.01) | |
| C09K 19/34 | (2006.01) | |
| G02B 5/30 | (2006.01) | |
| C08F 222/10 | (2006.01) | |
| C08F 22/20 | (2006.01) | |
| C09K 19/58 | (2006.01) | |
| C09K 19/04 | (2006.01) | |
| G02B 1/08 | (2006.01) | |

(52) U.S. Cl.
CPC ........ *C09K 19/3857* (2013.01); *C07D 241/04* (2013.01); *C07D 295/205* (2013.01); *C08F 22/20* (2013.01); *C08F 222/1006* (2013.01); *C09K 19/3483* (2013.01); *C09K 19/38* (2013.01); *C09K 19/586* (2013.01); *G02B 5/3016* (2013.01); *C08F 222/1061* (2020.02); *C08F 222/1065* (2020.02); *C08F 2810/20* (2013.01); *C09K 2019/0448* (2013.01); *G02B 1/08* (2013.01); *G02B 5/3083* (2013.01)

(58) Field of Classification Search
None
See application file for complete search history.

(56) References Cited

U.S. PATENT DOCUMENTS

| | | | | |
|---|---|---|---|---|
| 2,945,860 | A | * | 7/1960 | Schmidt-Barbo et al. ................. C07D 295/205 544/389 |
| 4,968,798 | A | * | 11/1990 | Gunther ............. C09K 19/3483 544/224 |
| 2006/0160851 | A1 | | 7/2006 | Ebdrup et al. |
| 2016/0318845 | A1 | * | 11/2016 | Katoh ..................... C07C 69/75 |

FOREIGN PATENT DOCUMENTS

| | | | |
|---|---|---|---|
| EP | 0 322 724 | A2 | 7/1989 |
| JP | 2006-124368 | A | 5/2006 |
| JP | 2008-239568 | A | 10/2008 |
| JP | 2008239568 | A * | 10/2008 |
| JP | 2011-075924 | A | 4/2011 |
| JP | 5082538 | B2 | 11/2012 |
| WO | 2004/111032 | A1 | 12/2004 |
| WO | 2015/115390 | A1 | 8/2015 |

OTHER PUBLICATIONS

English translation of JP2008239568. (Year: 2008).*
International Search Report dated Nov. 29, 2016, in counterpart International Application No. PCT/JP2016/077200.
Written Opinion of the International Searching Authority dated Nov. 29, 2016, in counterpart International Application No. PCT/JP2016/077200.
International Preliminary Report on Patentability dated Apr. 11, 2017, in counterpart International Application No. PCT/JP2016/077200.

* cited by examiner

*Primary Examiner* — Chanceity N Ribonson
*Assistant Examiner* — Anna Malloy
(74) *Attorney, Agent, or Firm* — Sughrue Mion, PLLC

(57) ABSTRACT

A polymerizable liquid crystal compound represented by Formula (I):

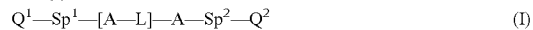

$$Q^1-Sp^1-[A-L]-A-Sp^2-Q^2 \quad (I)$$

A represents a divalent nitrogen-containing saturated cyclic group (that may have a substituent) formed by removing two hydrogen atoms from piperidine or piperazine, a phenylene group that may have a substituent, or a trans-1,4-cyclohexylene group that may have a substituent; L represents a linking group such as —C(=O)O— or —OC(=O)—; m represents 3 to 12; $Sp^1$ and $Sp^2$ represent an alkylene group having 1 to 20 carbon atoms; any one of $Q^1$ and $Q^2$ represents a polymerizable group; and Formula (I) has a nitrogen-containing saturated cyclic group and a phenylene group that are directly bonded to each other via —C(=O)O—. By using a polymerizable composition including the polymerizable liquid crystal compound, a film such as a retardation film can have low birefringence or a reflection film can have high selectivity in a reflection wavelength range.

18 Claims, No Drawings

POLYMERIZABLE LIQUID CRYSTAL COMPOUND, POLYMERIZABLE COMPOSITION, AND FILM

CROSS-REFERENCE TO RELATED APPLICATIONS

This application is a continuation of PCT International Application No. PCT/JP2016/077200 filed on Sep. 15, 2016, which claims priority under 35 U.S.C § 119 (a) to Japanese Patent Application No. 2015-184756 filed on Sep. 18, 2015, the entire content of which is incorporated herein by reference.

BACKGROUND OF THE INVENTION

1. Field of the Invention

The present invention relates to a novel polymerizable liquid crystal compound. The present invention also relates to a polymerizable composition including the polymerizable liquid crystal compound and a film manufactured by using the polymerizable composition.

2. Description of the Related Art

Various optical films such as a retardation film and a reflection film can be produced by using a polymerizable liquid crystal compound. A birefringence of the polymerizable liquid crystal compound is one of the properties greatly relating to the optical properties of the obtained optical film. For example, a reflection film having high selectivity in a reflection wavelength range can be obtained by using a film obtained by fixing a cholesteric liquid crystalline phase formed by using a polymerizable liquid crystal compound having low birefringence. WO2015/115390A discloses a liquid crystal compound having a divalent saturated hydrocarbon ring group in a mesogen portion as a polymerizable liquid crystal compound having low birefringence.

SUMMARY OF THE INVENTION

An object of the present invention is to provide a novel polymerizable liquid crystal compound having low birefringence. Another object of the present invention is to provide a film such as a retardation film having low birefringence or a reflection film having high selectivity in a reflection wavelength range.

The present inventors have conducted research in various ways in order to achieve the above objects and have found that a polymerizable liquid crystal compound including a saturated ring including nitrogen together with a phenylene group in a mesogen exhibited liquid crystallinity and lower birefringence than a polymerizable liquid crystal compound in which the mesogen is formed of only aromatic rings. As a compound used as a component of a polymerizable liquid crystal composition, a compound including a saturated ring including nitrogen together with a phenylene group is disclosed in JP5082538B. However, the present inventors have checked that the compound exemplified in JP5082538B did not have sufficient liquid crystallinity. Based on this knowledge, the present inventors have further conducted research so as to complete the present invention.

That is, the present invention is to provide <1> to <14> below.

<1> A polymerizable liquid crystal compound represented by Formula (I):

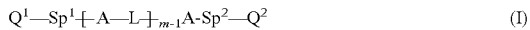

in Formula (I),

A represents a nitrogen-containing saturated cyclic group that may have a substituent, a phenylene group that may have a substituent, or a trans-1,4-cyclohexylene group that may have a substituent, in which the nitrogen-containing saturated cyclic group is a divalent group formed by removing two hydrogen atoms from piperidine or piperazine, L represents a single bond, or a linking group selected from the group consisting of —$CH_2$O—, —O$CH_2$—, —($CH_2$)$_2$OC(=O)—, —C(=O)O($CH_2$)$_2$—, —C(=O)O—, —OC(=O)—, —OC(=O)O—, —CH=CH—C(=O)O—, and —OC(=O)—CH=CH—, m represents an integer of 3 to 12, $Sp^1$ and $Sp^2$ each independently represent a single bond or a linking group selected from the group consisting of a linear or branched alkylene group having 1 to 20 carbon atoms and a group in which one or more —$CH_2$—'s in a linear or branched alkylene group having 1 to 20 carbon atoms are substituted with —O—, —S—, —NH—, —N($CH_3$)—, —C(=O)—, —OC(=O)—, or —C(=O)O—, and $Q^1$ and $Q^2$ each independently represent a hydrogen atom or a polymerizable group selected from the group consisting of groups represented by Formulae Q-1 to Q-5, here, any one of $Q^1$ and $Q^2$ represent a polymerizable group;

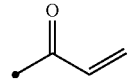

Q-1

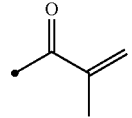

Q-2

Q-3

Q-4

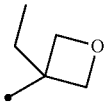

Q-5

Formula (I) includes a partial structure represented by Formula (V): and

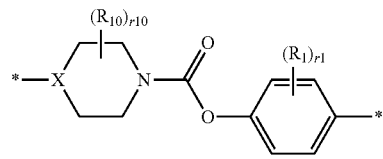

Formula (V)

in the formula, X represents N or CH, $R_1$ represents a substituent, $R_{10}$ represents a substituent, r1 and r10 each independently represent an integer of 0 to 4, a plurality of $R_1$'s in a case where r1 is 2 to 4 may be identical to or different from each other, a plurality of $R_{10}$'s in a case where r10 is 2 to 4 may be identical to or different from each other, and * represents a bonding site to another portion of Formula (I).

<2> The polymerizable liquid crystal compound according to <1>, in which at least one of a phenylene group that is substituted with a group represented by —C(=O)—$X^3$—$Sp^3$—$Q^3$ or a trans-1,4-cyclohexylene group that is substituted with a group represented by —C(=O)—$X^3$—$Sp^3$—$Q^3$ is included as A, here, $X^3$ represents a single bond, —O—, —S—, or —N($Sp^4$—$Q^4$)—, or a nitrogen atom that forms a ring structure together with $Q^3$ and $Sp^3$, $Sp^3$ and $Sp^4$ each independently represent a single bond and a linking group selected from the group consisting of a linear or branched alkylene group having 1 to 20 carbon atoms and a group in which one or more —$CH_2$—'s in a linear or branched alkylene group having 1 to 20 carbon atoms are substituted with —O—, —S—, —NH—, —N($CH_3$)—, —C(=O)—, —OC(=O)—, or —C(=O)O—, and $Q^3$ and $Q^4$ each independently represent a hydrogen atom, a cycloalkyl group, a group in which one or more —$CH_2$—'s in a cycloalkyl group are substituted with —O—, —S—, —NH—, —N($CH_3$)—, —C(=O)—, —OC(=O)—, or —C(=O)O—, or any one polymerizable group selected from the group consisting of groups represented by Formulae Q-1 to Q-5.

<3> The polymerizable liquid crystal compound according to <2>, in which $R_1$ is a group represented by —C(=O)—$X^3$—$Sp^3$—$Q^3$.

<4> The polymerizable liquid crystal compound according to <2> or <3>, in which $X^3$ is —O—, $Sp^3$ is a linear or branched alkylene group having 1 to 20 carbon atoms, and $Q^3$ is a hydrogen atom.

<5> The polymerizable liquid crystal compound according to any one of <1> to <4>, in which Formula (I) includes a partial structure represented by Formula (V-1),

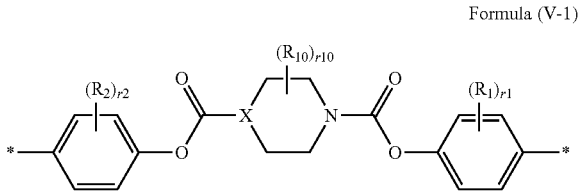

Formula (V-1)

in the formula, X represents N or CH, $R_1$ and $R_2$ each independently represent a substituent, $R_{10}$ represents a substituent, r1, r2, and r10 each independently represent an integer of 0 to 4, a plurality of $R_1$'s in a case where r1 is 2 to 4 may be identical to or different from each other, a plurality of $R_2$'s in a case where r2 is 2 to 4 may be identical to or different from each other, a plurality of $R_{10}$'s in a case where r10 is 2 to 4 may be identical to or different from each other, and * represents a bonding site to another portion of Formula (I).

<6> The polymerizable liquid crystal compound according to any one of <1> to <5>, in which $R_{10}$ is an alkyl group having 1 to 5 carbon atoms.

<7> The polymerizable liquid crystal compound according to any one of <1> to <6>, in which, in Formula (I), substituents that may be included in the phenylene group and the trans-1,4-cyclohexylene group are selected from the group consisting of an alkyl group, an alkoxy group, and a group represented by —C(=O)—$X^3$—$Sp^3$—$Q^3$, here, $X^3$ represents a single bond, —O—, —S—, or —N($Sp^4$—$Q^4$)—, or a nitrogen atom that forms a ring structure together with $Q^3$ and $Sp^3$, $Sp^3$ and $Sp^4$ each independently represent a single bond and a linking group selected from the group consisting of a linear or branched alkylene group having 1 to 20 carbon atoms and a group in which one or more —$CH_2$—'s in a linear or branched alkylene group having 1 to 20 carbon atoms are substituted with —O—, —S—, —NH—, —N($CH_3$)—, —C(=O)—, —OC(=O)—, or —C(=O)O—, and $Q^3$ and $Q^4$ each independently represent a hydrogen atom, a cycloalkyl group, a group in which one or more —$CH_2$—'s in a cycloalkyl group are substituted with —O—, —S—, —NH—, —N($CH_3$)—, —C(=O)—, —OC(=O)—, or —C(=O)O—, or any one polymerizable group selected from the group consisting of groups represented by Formulae Q-1 to Q-5.

<8> The polymerizable liquid crystal compound according to any one of <1> to <7>, in which all of L's represent linking groups selected from the group consisting of —C(=O)O— and —OC(=O)—.

<9> A polymerizable composition comprising: the polymerizable liquid crystal compound according to any one of <1> to <8>.

<10> The polymerizable composition according to <9>, in which the polymerizable liquid crystal compound is included by 10 mass % or greater with respect to a total mass of the polymerizable liquid crystal compound.

<11> The polymerizable composition according to <9> or <10>, further comprising: a crosslinking agent.

<12> The polymerizable composition according to any one of <9> to <11>, further comprising: a polymerization initiator.

<13> The polymerizable composition according to any one of <9> to <12>, further comprising: a chiral compound.

<14> A film comprising: a layer obtained by curing the polymerizable composition according to any one of <9> to <13>.

The present invention is to provide a novel polymerizable liquid crystal compound. It is possible to provide a film such as a retardation film having low birefringence or a reflection film having high selectivity in a reflection wavelength range by using a polymerizable composition including the polymerizable liquid crystal compound.

DESCRIPTION OF THE PREFERRED EMBODIMENTS

Hereinafter, the present invention is specifically described. In the present specification, the numerical range expressed by using "to" means a range including numerical values described before and after "to" as a lower limit value and an upper limit value.

In the present specification, the expression "(meth)acrylate" means "any one or both of acrylate and methacrylate". The same is applied to a "(meth)acrylic group", and a "(meth)acryloyl group" means "any one or both of an acryloyl group and a methacryloyl group".

In the present specification, the expression "liquid crystal layer" means a layer formed by using a polymerizable composition including a polymerizable liquid crystal compound and particularly means a layer obtained by curing a polymerizable composition including a polymerizable liquid crystal compound. With respect to the liquid crystal layer, it is sufficient that optical properties of the liquid crystalline phase are maintained in the layer, and the composition in the cured film finally is not necessary to exhibit liquid crystallinity. For example, the composition may be caused to have high molecular weight due to curing reaction to lose liquid crystallinity.

In the present specification, the expression "retardation" means in-plane retardation, and means in-plane retardation in a wavelength of 550 nm, in a case where a wavelength is not mentioned. In the present specification, the in-plane retardation is measured by using a polarization retardation analyzer AxoScan manufactured by AXOMETRICS, Inc. The in-plane retardation at a wavelength of λ nm can also be measured by causing light of wavelength λ nm incident on KOBRA 21ADH or WR (manufactured by Oji Scientific Instruments Co., Ltd.) in the film normal direction.

In a case of "that may have a substituent" in the present specification, the substituent is not particularly limited, and examples thereof include a substituent selected from the group consisting of an alkyl group, a cycloalkyl group, an alkoxy group, an alkyl ether group, an amide group, an amino group, a halogen atom, and a group obtained by combining two or more of the above substituents. Examples of the substituent include a substituent represented by —C(=O)—$X^3$—$Sp^3$—$Q^3$ below.

In the present specification, an alkyl group may have a linear or branched chain shape. The number of carbon atoms of the alkyl group is preferably 1 to 30, more preferably 1 to 10, and particularly preferably 1 to 6. Examples of the alkyl group include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a 1,1-dimethylpropyl group, an n-hexyl group, an isohexyl group, a linear or branched heptyl group, an octyl group, a nonyl group, a decyl group, an undecyl group, and a dodecyl group. The above description regarding the alkyl group is also applied to an alkoxy group containing an alkyl group. In the present specification, specific examples of the alkylene group in a case of being referred to as an alkylene group include a divalent group obtained by removing one arbitrary hydrogen atom from each of the above examples of the alkyl group. Examples of the halogen atom include a fluorine atom, a chlorine atom, a bromine atom, and an iodine atom.

In the present specification, the number of carbon atoms of the cycloalkyl group is preferably 3 to 20, more preferably 5 or greater, preferably 10 or less, more preferably 8 or less, and even more preferably 6 or less. Examples of cycloalkyl groups include a cyclopropyl group, a cyclobutyl group, a cyclopentyl group, a cyclohexyl group, a cycloheptyl group, and a cyclooctyl group.

<Polymerizable Liquid Crystal Compound>

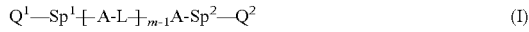
$$Q^1-Sp^1-(A-L)_{m-1}A-Sp^2-Q^2 \quad (I)$$

The polymerizable liquid crystal compound represented by Formula (I) has m cyclic divalent groups A that may have a substituent.

m represents an integer of 3 to 12, preferably an integer of 3 to 9, and more preferably an integer of 3 to 5.

m A's may be identical to or different from each other. The cyclic divalent group represented by A is a nitrogen-containing saturated cyclic group that may have a substituent, a phenylene group that may have a substituent, or a trans-1,4-cyclohexylene group that may have a substituent. A phenylene group is preferably a 1,4-phenylene group.

In the present specification, a "nitrogen-containing saturated cyclic group" is a divalent group formed by removing two hydrogen atoms (hydrogen radicals) from piperidine or piperazine. Positions at which two hydrogen atoms are removed are not particularly limited, but it is preferable that the positions are not the same carbon atoms or hydrogen atoms bonded to an adjacent atom, and it is more preferable that the position is a hydrogen atom at 1-position and a hydrogen atom at 4-position.

With respect to m A's, it is preferable that a nitrogen-containing saturated cyclic group that may have a substituent in the center, and the same cyclic divalent groups or the same combinations of cyclic divalent groups may exist on both sides thereof. It is preferable that the polymerizable liquid crystal compound represented by Formula (I) has a structure in which a) a phenylene group, a phenylene group, a nitrogen-containing saturated cyclic group, a phenylene group, and a phenylene group; or b) a trans-1,4-cyclohexylene group, a phenylene group, a nitrogen-containing saturated cyclic group, a phenylene group, and a trans-1,4-cyclohexylene group are arranged in this order. In a) or b), each of the cyclic divalent groups may have a substituent. In a) to c), it is also preferable that a cyclic divalent group at a terminal is unsubstituted.

A nitrogen-containing saturated cyclic group, a phenylene group, and a trans-1,4-cyclohexylene group may have one to four substituents. In a case where two or more substituents are included, the two or more substituents may be identical to or different from each other. It is preferable that the nitrogen-containing saturated cyclic group has one substituent or is unsubstituted. It is preferable that the phenylene group has one or two substituents or is unsubstituted, and it is more preferable that the phenylene group has only one substituent or is unsubstituted. It is preferable that the trans-1,4-cyclohexylene group is unsubstituted.

The substituents that may be included in the phenylene group and the trans-1,4-cyclohexylene group are preferably substituents selected from the group consisting of an alkyl group, an alkoxy group, and —C(=O)—$X^3$—$Sp^3$—$Q^3$. Here, $X^3$ represents a single bond, —O—, —S—, or —N($Sp^4$—$Q^4$)—, or represents a nitrogen atom that forms a ring structure together with $Q^3$ and $Sp^3$. $Sp^3$ and $Sp^4$ each independently represent a single bond or a linking group selected from the group consisting of a linear or branched alkylene group having 1 to 20 carbon atoms and a group in which one or more —$CH_2$—'s in a linear or branched alkylene group having 1 to 20 carbon atoms are substituted with —O—, —S—, —NH—, —N($CH_3$)—, —C(=O)—, —OC(=O)—, or —C(=O)O—.

$Q^3$ and $Q^4$ each independently represent a hydrogen atom, a cycloalkyl group, a group in which one or more —$CH_2$—'s in a cycloalkyl group are substituted with —O—, —S—, —NH—, —N($CH_3$)—, —C(=O)—, —OC(=O)—, or —C(=O)O—, or any one polymerizable group selected from the group consisting of groups represented by Formulae Q-1 to Q-5.

Specific examples of the group in which one or more —$CH_2$—'s in the cycloalkyl group are substituted with —O—, —S—, —NH—, —N($CH_3$)—, —C(=O)—, —OC(=O)—, or —C(=O)O— include a tetrahydrofuranyl group, a pyrrolidinyl group, an imidazolidinyl group, a pyrazolidinyl group, a piperidyl group, a piperazinyl group, and a morpholinyl group. The substitution position is not particularly limited. Among these, a tetrahydrofuranyl group is preferable, and a 2-tetrahydrofuranyl group is particularly preferable.

As the substituents that may be included in the phenylene group and the trans-1,4-cyclohexylene group, —C(=O)—$X^3$—$Sp^3$—$Q^3$ particularly preferable, and —C(=O)—$X^3$—$Sp^3$—$Q^3$ in which $X^3$ is —O—, $Sp^3$ is a linear or branched alkylene group having 1 to 20 carbon atoms, $Q^3$ is a hydrogen atom is preferable. In this case, $Sp^3$ is more preferably a linear or branched alkylene group having 1 to 5 carbon atoms and even more preferably a linear or branched alkylene group having 1 to 3 carbon atoms.

The substituent in a case where the nitrogen-containing saturated cyclic group has a substituent is preferably an alkyl group having 1 to 5 carbon atoms, more preferably an alkyl group having 1 to 3 carbon atoms, and even more preferably a methyl group or an ethyl group.

The polymerizable liquid crystal compound represented by Formula (I) includes a divalent nitrogen-containing saturated cyclic group that may have at least one substituent and a phenylene group that may have at least one substituent. More specifically, Formula (I) includes at least a partial structure represented by Formula (V):

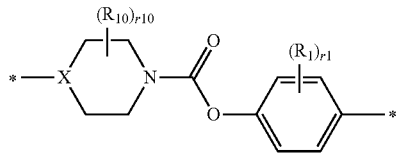

Formula (V)

in the formula, X represents N or CH, $R_1$ represents a substituent, $R_{10}$ represents a substituent, each of r1 and r10 represents an integer of 0 to 4, a plurality of $R_1$'s in a case where r1 is 2 to 4 may be identical to or different from each other, a plurality of $R_{10}$'s in a case where r10 is 2 to 4 may be identical to or different from each other, and * represents a bonding site to another portion of Formula (I).

$R_1$ is preferably a substituent selected from the group consisting of an alkyl group, an alkoxy group, and —C(=O)—$X^3$—$Sp^3$—$Q^3$ and particularly preferably —C(=O)—$X^3$—$Sp^3$—$Q^3$. r1 is preferably 0 to 2 and particularly preferably 1. $R_{10}$ is preferably an alkyl group having 1 to 5 carbon atoms, more preferably an alkyl group having 1 to 3 carbon atoms, and particularly preferably a methyl group or an ethyl group. r10 is preferably 0 to 2 and more preferably 0 or 1.

It is preferable that Formula (I) further includes at least a partial structure represented by Formula (V-1). Formula (V-1) includes Formula (V) in the formula.

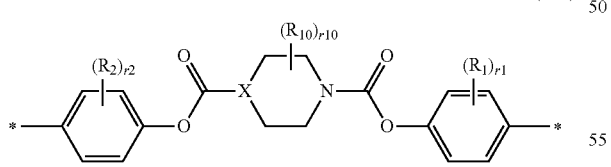

Formula (V-1)

In the formula, X, $R_1$, $R_{10}$, r1, r10, and * each have the same meaning as those in Formula (V). $R_2$ represents a substituent, each of r2's an integer of 0 to 4, and a plurality of $R_2$'s in a case where r2 is 2 to 4 may be identical to or different from each other.

$R_2$ is preferably a substituent selected from the group consisting of an alkyl group, an alkoxy group, and —C(=O)—$X^3$—$Sp^3$—$Q^3$ and particularly preferably —C(=O)—$X^3$—$Sp^3$—$Q^3$. r2 is preferably 0 to 2 and particularly preferably 1.

It is also preferable that $R_1$ and $R_2$ are identical to each other and r1 and r2 are identical to each other.

In Formula (I), L represents a single bond, or a linking group selected from the group consisting of —CH$_2$O—, —OCH$_2$—, —(CH$_2$)$_2$OC(=O)—, —C(=O)O(CH$_2$)$_2$—, —C(=O)O—, —OC(=O)—, —OC(=O)O—, —CH=CH—C(=O)O—, and —OC(=O)—CH=CH—. It is preferable that L is —C(=O)O— or —OC(=O)—, and it is more preferable that all of L's are —C(=O)O— or —OC(=O)—. m L's may be identical to or different from each other.

In Formula (I), $Sp^1$ and $Sp^2$ each independently represent a single bond or a linking group selected from the group consisting of a linear or branched alkylene group having 1 to 20 carbon atoms and a group in which one or more —CH$_2$—'s in a linear or branched alkylene group having 1 to 20 carbon atoms are substituted with —O—, —S—, —NH—, —N(CH$_3$)—, —C(=O)—, —OC(=O)—, or —C(=)O—. $Sp^1$ and $Sp^2$ are each independently and preferably a linear alkylene group having 1 to 10 carbon atoms in which linking groups selected from the group consisting of —O—, —OC(=O)—, and —C(=O)O— are bonded to both terminals and a linking group formed by combining one or more groups selected from the group consisting of —OC(=O)—, —C(=O)O—, —O—, and a linear alkylene group having 1 to 10 carbon atoms and more preferably a linear alkylene group having 1 to 10 carbon atoms in which linking groups selected from the group consisting of —O—, —OC(=O)—, and —C(=O)O— are bonded to both terminals.

$Q^1$ and $Q^2$ each independently represent a hydrogen atom or a polymerizable group selected from the group consisting of groups represented by Formulae Q-1 to Q-5. Here, any one of $Q^1$ and $Q^2$ represents a polymerizable group.

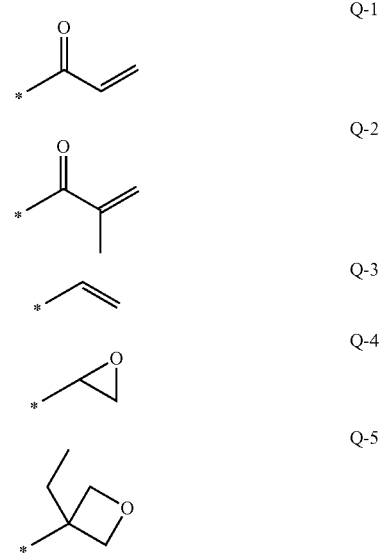

The polymerizable group is preferably an acryloyl group (Formula Q-1) or a methacryloyl group (Formula Q-2).

The polymerizable liquid crystal compound represented by Formula (I) can be manufactured by the well-known methods, and for example, the polymerizable liquid crystal compound can be manufactured by the following method.

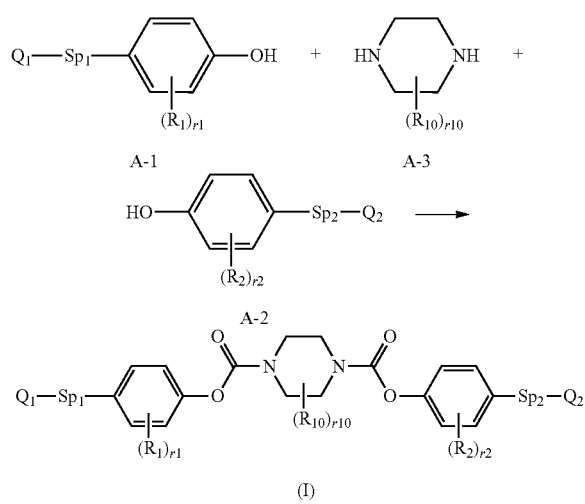

For example, in Formula (I), L is —C(=O)O—, the polymerizable liquid crystal compound can be manufactured by carbamation by using phenol (or alcohol) derivatives A-1 and A-2 and a piperazine derivative A-3. Examples of the method of the carbamation reaction include a method of causing the piperazine derivative A-3 to carbamoyl chloride using triphosgene or the like and causing the phenol (or alcohol) derivatives A-1 and A-2 to act in the presence of a base and a method of causing the phenol (or alcohol) derivatives A-1 and A-2 to chloroformate using triphosgene or the like and causing the piperazine derivative A-3 to act in the presence of a base.

The polymerizable liquid crystal compound represented by Formula (I) has low birefringence. For example, the polymerizable liquid crystal compound has a lower birefringence than a polymerizable liquid crystal compound having the same number of phenylene groups as cyclic divalent groups. The polymerizable liquid crystal compound represented by Formula (I) has high stability under high temperature and high humidity.

Regardless of types of substituents or linking groups, since absorption in the visible light region is extremely small, the polymerizable liquid crystal compound represented by Formula (I) satisfies a plurality of characteristics of being colorless and transparent, having a wide liquid crystalline phase range, being easily dissolved in a solvent, and being easily polymerized. Based on this, the cured film produced by using the polymerizable composition containing the polymerizable liquid crystal compound represented by Formula (I) can satisfy a plurality of characteristics of sufficient hardness, colorlessness and transparency, and satisfactory weather fastness and heat resistance. Particularly, a cured film manufactured by using a polymerizable composition including the polymerizable liquid crystal compound represented by Formula (I) has high durability under high temperature and high humidity. The cured film formed using the polymerizable composition can be used in various applications such as a retardation plate which is a constitutional element of an optical element, a polarizing element, a selective reflection film, a color filter, an antireflection film, a view angle compensation film, holography, and an alignment film, in various environments.

<Polymerizable Composition>

The polymerizable composition including the polymerizable liquid crystal compound represented by Formula (I) of the present invention may include one or more polymerizable liquid crystal compounds represented by Formula (I).

The total amount of the polymerizable liquid crystal compound represented by Formula (I) in the polymerizable composition including the polymerizable liquid crystal compound represented by Formula (I) is not particularly limited, but may be 10 mass % or greater, preferably 30 mass % or greater, more preferably 50 mass % or greater, and even more preferably 70 mass % or greater with respect to the solid content mass of the polymerizable composition. The upper limit may be 100 mass %, 99 mass % or less, 95 mass % or less, and 90 mass %.

The polymerizable composition including the polymerizable liquid crystal compound represented by Formula (I) may include other components such as other liquid crystal compounds, a chiral compound, a polymerization initiator, and an alignment control agent, in addition to the polymerizable liquid crystal compounds represented by Formula (I). Hereinafter, each of the components is described.

[Other Liquid Crystal Compounds]

The polymerizable composition may contain one or more different liquid crystal compounds together with the polymerizable liquid crystal compound represented by Formula (I). The polymerizable liquid crystal compound represented by Formula (I) has high compatibility with other liquid crystal compounds, and thus it is possible to form a film with high transparency without causing opaqueness or the like even in a case where other liquid crystal compounds are mixed. Since other liquid crystal compounds are used together, it is possible to provide compositions in various compositions which are suitable for various applications. Examples of other liquid crystal compounds that can be used in combination include rod-like nematic liquid crystal compounds. Examples of the rod-like nematic liquid crystal compound include azomethines, azoxys, cyanobiphenyls, cyanophenyl esters, benzoic acid esters, phenyl cyclohexane carboxylic acid esters, cyanophenyl cyclohexanes, cyano-substituted phenyl pyrimidines, alkoxy-substituted phenyl pyrimidines, phenyl dioxanes, tolanes, and alkenyl cyclohexyl benzonitriles. It is possible to use not only low molecular weight liquid crystal compounds as described above but also high molecular weight liquid crystal compounds.

The other liquid crystal compounds may be polymerizable or non-polymerizable. The rod-like liquid crystal compounds not having a polymerizable group are disclosed in various documents (for example, Y. Goto et. al., Mol. Cryst. Liq. Cryst. 1995, Vol. 260, pp. 23 to 28).

The polymerizable rod-like liquid crystal compound can be obtained by introducing the polymerizable group to the rod-like liquid crystal compound. Examples of the polymerizable group include an unsaturated polymerizable group, an epoxy group, and an aziridinyl group, an unsaturated polymerizable group is preferable, and an ethylenically unsaturated polymerizable group is particularly preferable. The polymerizable group is introduced to a molecule of a rod-like liquid crystal compound in various methods. The number of polymerizable groups included in the polymerizable rod-like liquid crystal compound is preferably 1 to 6 and more preferably 1 to 3. Examples of the polymerizable rod-like liquid crystal compounds include compounds disclosed in Makromol. Chem., Vol. 190, page 2,255 (1989), Advanced Materials Vol. 5, page 107 (1993), U.S. Pat. Nos. 4,683,327A; 5,622,648A; and 5,770,107A, WO95/22586A, WO95/24455A, WO97/00600A, WO98/23580A, WO98/52905A, JP1989-272551A (JP-H01-272551A), JP1994-16616A (JP-H06-16616A), JP1995-110469A (JP-H07-

110469A), JP1999-80081A (JP-H11-80081A), and JP2001-328973A. Two or more kinds of polymerizable rod-like liquid crystal compounds may be used together. In a case where two or more kinds of polymerizable rod-like liquid crystal compounds are used together, the alignment temperature can be decreased.

The addition amount of the liquid crystal compound is not particularly limited, and is preferably 0 to 70 mass %, more preferably 0 to 50 mass %, and even more preferably 0 to 30 mass % with respect to a solid content mass of the polymerizable composition. However, the range thereof is not limited thereto. In the polymerizable composition, a mass ratio (a mass of the polymerizable liquid crystal compound represented by Formula (I)/a mass of other liquid crystal compounds) between the polymerizable liquid crystal compound represented by Formula (I) and other liquid crystal compounds may be 100/0 to 30/70, preferably 100/0 to 50/50, and more preferably 100/0 to 70/30. The ratio can be adjusted in a preferable range.

[Chiral Compound]

The polymerizable composition may include a chiral compound. In a case where the chiral compound is used, the polymerizable composition can be prepared as a composition exhibiting a cholesteric liquid crystalline phase. The chiral compound may be liquid crystalline or may be non-liquid crystalline. The chiral compound can be selected from various well-known chiral agents (for example, chiral agents, isosorbide derivatives, isomannide derivatives, and binaphthyl derivatives disclosed in Liquid Crystal Device Handbook, Chapter 3, Sections. 4 to 3, Chiral agent for TN and STN, page 199, Japan Society for the Promotion of Science edited by the 142nd committee in 1989). In general, the chiral compound includes an asymmetric carbon atom, but an axial asymmetric compound or a planar asymmetric compound which does not include the asymmetric carbon atom can be used. In an example of the axial asymmetric compound or the planar asymmetric compound, binaphthyl, helicene, paracyclophane, and a derivative thereof are included. The chiral compound (chiral agent) may have a polymerizable group. In a case where the chiral compound has a polymerizable group and the rod-like liquid crystal compound used together also has a polymerizable group, a polymer having a repeating unit derived from the rod-like liquid crystal compound and a repeating unit derived from the chiral compound can be formed by a polymerization reaction between the polymerizable chiral compound and the polymerizable rod-like liquid crystal compound. Therefore, the polymerizable group included in the polymerizable chiral compound is preferably a group which is the same as a polymerizable rod-like liquid crystal compound, particularly a polymerizable group included in the polymerizable liquid crystal compound represented by Formula (I). Accordingly, the polymerizable group of the chiral compound is also preferably an unsaturated polymerizable group, an epoxy group, an oxetanyl group, or an aziridinyl group, is more preferably a polymerizable group selected from the group consisting of groups represented by Formulae Q-1 to Q-5 and more preferably an acryloyl group (Formula Q-1) or a methacryloyl group (Formula Q-2).

In the polymerizable composition, the chiral compound is preferably 0.5 to 30 mass % with respect to a liquid crystal compound including the polymerizable liquid crystal compound represented by Formula (I). The use amount of the chiral compound is preferably smaller since as the use amount is smaller, an influence on liquid crystallinity is smaller. As a chiral compound, a compound having a strong twisting power such that twisted alignment with a desired helical pitch can be achieved even in a small amount is preferable. In this manner, examples of the chiral agent showing strong twisting power include chiral agents disclosed in JP2003-287623A. Examples thereof include chiral agents disclosed in JP2002-302487A, JP2002-80478A, JP2002-80851A, and JP2014-034581A, and LC-756 manufactured by BASF SE.

A film formed by causing a polymerizable composition in an aspect of containing a chiral compound to have a cholesteric liquid crystalline phase and fixing the polymerizable composition exhibits selective reflection characteristics with respect to light of a predetermined wavelength depending on its helical pitch, and is useful as a reflection film (for example, a visible light reflection film or an infrared reflection film). In a case where the polymerizable liquid crystal compound represented by Formula (I) exhibiting low birefringence is used, there is an advantage in that a reflection wavelength range becomes narrower compared with a film having the same thickness using a liquid crystal compound having higher birefringence and thus selectivity increases.

[Polymerization Initiator]

It is preferable that the polymerizable composition contains a polymerization initiator. For example, in an aspect of proceeding curing reaction by irradiation with ultraviolet rays and forming a cured film, it is preferable that a polymerization initiator to be used is a photopolymerization initiator that can start polymerization reaction due to irradiation with ultraviolet rays. Examples of the photopolymerization initiator include an α-carbonyl compound (disclosed in U.S. Pat. Nos. 2,367,661A and 2,367,670A), acyloin ether (disclosed in U.S. Pat. No. 2,448,828A), an α-hydrocarbon substituted aromatic acyloin compound (disclosed in U.S. Pat. No. 2,722,512A), a polynuclear quinone compound (disclosed in U.S. Pat. Nos. 3,046,127A and 2,951,758A), a combination of triarylimidazole dimer and p-aminophenylketone (disclosed in U.S. Pat. No. 3,549,367A), acridine and phenazine compounds (disclosed in JP1985-105667A (JP-S60-105667A) and U.S. Pat. No. 4,239,850A), an acylphosphine oxide compound (disclosed in JP1988-40799B (JP-S63-40799B), JP1993-29234B (JP-H05-29234B), JP1998-95788A (JP-H10-95788A), JP1998-29997A (JP-H10-29997A), JP2001-233842A, JP2000-80068A, JP2006-342166A, JP2013-114249A, JP2014-137466A, JP4223071B, JP2010-262028A, and JP2014-500852A), an oxime compound (disclosed in JP2000-66385A and JP4454067B), and an oxadiazole compound (disclosed in U.S. Pat. No. 4,212,970A). For example, disclosure in paragraphs 0500 to 0547 of JP2012-208494A can be referred to.

As the polymerization initiator, it is preferable to use an acylphosphine oxide compound or an oxime compound.

As the acylphosphine oxide compound, for example, IRGACURE 819 (compound name: bis(2,4,6-trimethylbenzoyl)-phenylphosphine oxide) manufactured by BASF Japan Ltd., which is a commercially available product, can be used. As the oxime compound, commercially available products of IRGACURE OXE01 (manufactured by BASF SE), IRGACURE OXE02 (manufactured by BASF SE), TR-PBG-304 (manufactured by Changzhou Tronly New Electronic Materials Co., Ltd.), ADEKA ARKLS NCI-831 and ADEKA ARKLS NCI-930 (manufactured by Adeka Corporation), and ADEKA ARKLS NCI-831 (manufactured by Adeka Corporation) can be used.

The polymerization initiator may be used singly, and two or more thereof may be used in combination.

The photopolymerization initiator is included in the polymerizable composition preferably by 0.1 to 20 mass % and more preferably by 1 to 8 mass % with respect to the solid content mass of the polymerizable composition.

[Alignment Control Agent]

An alignment control agent that contributes to the stable or prompt forming of a liquid crystalline phase (for example, a cholesteric liquid crystalline phase) may be added to the polymerizable composition. Examples of the alignment control agent include a fluorine-containing (meth)acrylate-based polymer, a compound represented by Formulas (X1) to (X3) disclosed in WO2011/162291A, and a compound disclosed in paragraphs [0020] to [0031] of JP2013-47204A. Examples thereof may further include two or more kinds selected from these alignment control agents. These compounds can reduce or substantially horizontally align the tilt angle the molecules of the liquid crystal compound at the air interface of the layer. In the present specification, the expression "horizontal alignment" means that a longer axis of the liquid crystal molecule and a film plane are parallel to each other, but the longer axis and the film plane do not have to be strictly parallel, and means alignment in which a tilt angle formed with a horizontal plane is less than 20°. In a case where the liquid crystal compound is horizontally aligned near the air interface, orientation defects are hardly generated, and thus transparency in a visible light region increases. On the other hand, when the molecules of the liquid crystal compound are aligned at a large tilt angle, for example, in the case of forming a cholesteric liquid crystalline phase, since the helical axis deviates from the film plane normal line, the reflectivity decreases or a fingerprint pattern is generated, and this causes an increase in haze or diffraction, and thus alignment at a large tilt angle is not preferable.

Examples of the fluorine-containing (meth)acrylate-based polymer that can be used as an alignment control agent are disclosed in [0018] to [0043] of JP2007-272185A.

As the alignment control agent, a compound may be used singly or two or more kinds of compounds may be used in combination.

In the polymerizable composition, the content of the alignment control agent is preferably 0.01 to 10 mass %, more preferably 0.01 to 5 mass %, and particularly preferably 0.02 to 1 mass % with respect to the mass of the compound of Formula (I).

[Crosslinking agent]

The polymerizable composition may arbitrarily contain a crosslinking agent in order to improve film hardness and durability after curing. As the crosslinking agent, an agent that is cured by ultraviolet rays, heat, humidity, and the like can be suitably used.

The crosslinking agent is not particularly limited and can be suitably selected depending on the purpose, and examples thereof include a polyfunctional acrylate compound such as trimethylolpropane tri(meth)acrylate, pentaerythritol tri (meth)acrylate, and pentaerythritol tetraacrylate; an epoxy compound such as glycidyl (meth)acrylate and ethylene glycol diglycidyl ether; an aziridine compound such as 2,2-bishydroxymethylbutanol-tris[3-(1-aziridinyl) propionate] and 4,4-bis(ethyleneiminocarbonylamino) diphenylmethane; an isocyanate compound such as hexamethylene diisocyanate and a biuret-type isocyanate; a polyoxazoline compound having an oxazoline group in a side chain thereof; and an alkoxysilane compound such as vinyl trimethoxysilane and N-(2-aminoethyl) 3-aminopropyltrimethoxysilane. In accordance with the reactivity of the crosslinking agent, a well-known catalyst can be used, and productivity can be improved in addition to improvement in film hardness and durability. These may be used singly, and two or more kinds thereof may be used in combination.

The content of the crosslinking agent is preferably 3 mass % to 20 mass % and more preferably 5 mass % to 15 mass % with respect to the solid content mass of the polymerizable composition. In a case where the content of the crosslinking agent is 3 mass % or greater, an effect of improving the crosslink density is high, and in a case where the content thereof is 20 mass % or less, the stability of the cholesteric liquid crystal layer is high.

[Other Additives]

The polymerizable composition may contain one or more kinds of other additives such as an antioxidant, an ultraviolet absorbing agent, a sensitizing agent, a stabilizer, a plasticizer, a chain transfer agent, a polymerization inhibitor, an antifoaming agent, a leveling agent, a thickener, a flame retardant, a surface-active substance, a dispersing agent, and a color material such as a dye or a pigment.

<Film>

The polymerizable composition including the polymerizable liquid crystal compound represented by Formula (I) of the present invention is useful as materials of various optical films such as a retardation film and a reflection film, and various optical films can be formed by using this polymerizable composition.

[Method of Manufacturing Film]

An example of the method of manufacturing the optical film is a manufacturing method at least including:

(i) coating a surface of a substrate or the like with a polymerizable composition and forming a state of a liquid crystalline phase (a nematic liquid crystalline phase, a cholesteric liquid crystalline phase, or the like), and (ii) proceeding curing reaction of a polymerizable composition, fixing the liquid crystalline phase, so as to form a cured film (liquid crystal layer).

The steps (i) and (ii) are repeated a plurality of times so as to produce a film obtained by laminating a plurality of the cured films. A film obtained by laminating a plurality of the cured films can be produced by bonding the plurality of cured films with an adhesive.

In the step (i), first, a substrate or a surface of an alignment film formed on the substrate is coated with a polymerizable composition. The polymerizable composition is preferably prepared by the coating solution obtained by dissolving and/or dispersing materials in the solvent. As a solvent used in the preparation of the coating solution, an organic solvent is preferably used. Examples of the organic solvent include amide (for example, N,N-dimethylformamide); sulfoxide (such as dimethylsulfoxide); a heterocyclic compound (for example, pyridine); hydrocarbon (for example, benzene and hexane); alkyl halide (for example, chloroform and dichloromethane); ester (for example, methyl acetate, butyl acetate, and propylene glycol monoethyl ether acetate); ketone (for example, acetone, methyl ethyl ketone, cyclohexanone, and cyclopentanone); ether (for example, tetrahydrofuran and 1,2-dimethoxyethane); and 1,4-butanediol diacetate. Among these, alkyl halide; esters, and ketone are particularly preferable. Two or more types of organic solvents may be used in combination.

The coating solution can be applied by various methods such as a wire bar coating method, an extrusion coating method, a direct gravure coating method, a reverse gravure coating method, and a die-coating method. The composition is ejected from a nozzle by using an ink jet device, and thus, a coating film can be formed.

Subsequently, the polymerizable composition that is applied to the surface and became a coating film is caused to be a state of a liquid crystalline phase such as a nematic liquid crystalline phase or a cholesteric liquid crystalline phase. For example, in an aspect in which the polymerizable composition is prepared as a coating solution containing a solvent, a state of the liquid crystalline phase can be obtained by drying the coating film and removing the solvent in some cases. In order to obtain the transition temperature to the liquid crystalline phase, the coating film may be heated, as desired. For example, first, the coating film is heated to a temperature of an isotropic phase, and then, is cooled to a transition temperature of a liquid crystalline phase, and thus, it is possible to stably obtain the state of the liquid crystalline phase. In view of manufacturing suitability or the like, the transition temperature of the liquid crystalline phase of the polymerizable composition is preferably in a range of 10° C. to 250° C. and is more preferably in a range of 10° C. to 150° C. In a case where the transition temperature of the liquid crystalline phase is lower than 10° C., a cooling step is necessary in order to decrease the temperature to a temperature range at which a liquid crystalline phase is exhibited. In a case where the transition temperature of the liquid crystalline phase is higher than 200° C., a high temperature is required to obtain an isotropic liquid state in a temperature which is even higher than the temperature range in which the liquid crystalline phase appears, and it may be disadvantageous in waste of thermal energy, deformation of the substrate, degeneration, and the like.

Subsequently, in the step (ii), a coating film that became in a state of a liquid crystalline phase is cured. The curing may proceed by any polymerization method such as a radical polymerization method, an anionic polymerization method, a cationic polymerization method, and a coordination polymerization method. According to the polymerizable liquid crystal compound represented by Formula (I), a suitable polymerization method is selected. According to this polymerization, a polymer having a unit derived from the polymerizable liquid crystal compound represented by Formula (I) in a constitutional unit can be obtained.

For example, the curing reaction proceeds by irradiation with ultraviolet rays. For ultraviolet irradiation, a light source such as an ultraviolet lamp is used. In this step, the curing reaction of the composition proceeds by the irradiation with ultraviolet rays, and a liquid crystalline phase (a nematic liquid crystalline phase, a cholesteric liquid crystalline phase, and the like) is fixed, so as to form a cured film (liquid crystal layer).

There is no particular limitation on the irradiation energy amount of ultraviolet rays, but is preferably about 0.1 J/cm$^2$ to 0.8 J/cm$^2$ generally. The time for irradiating the coating film with ultraviolet rays is not particularly limited, but may be determined in view of both sufficient strength and productivity of the cured film.

In order to promote curing reaction, ultraviolet irradiation under the heating condition may be performed. The temperature during ultraviolet irradiation is preferably maintained in the temperature range that exhibits the liquid crystalline phase such that the liquid crystalline phase is not collapsed. An oxygen concentration in the atmosphere is involved in a degree of polymerization, and does not reach a desired degree of polymerization in the air, and in a case where film hardness is insufficient, it is preferable to decrease the oxygen concentration in the atmosphere by a method such as nitrogen substitution.

In the above step, the liquid crystalline phase is fixed, so as to form a cured film. Here, with respect to a state in which the liquid crystalline phase is "fixed", an aspect in which the alignment of the compound which is in the liquid crystalline phase is maintained is the most typical and preferable aspect. The state is not limited thereto and specifically indicates a state in which the fixed alignment shape can be stably and continuously maintained without fluidity in a layer or without a change in the shape of the alignment due to an external field or an external force, in a temperature range of generally 0° C. to 50° C. and in a temperature range of −30° C. to 70° C. under more rigorous conditions. According to the present invention, it is preferable that the alignment state of the liquid crystalline phase is fixed by the curing reaction performed by irradiation with ultraviolet rays.

The thickness of the cured film is not particularly limited. According to the application or according to desired optical characteristics, a preferable film thickness may be determined. Generally, the thickness is preferably 0.05 to 50 μm and more preferably 1 to 35 μm.

[Substrate]

The film may have a substrate. The substrate has self-supporting properties, as long as the substrate supports the above cured film, there is no limitation on materials and optical characteristics. The substrate can be selected from a glass plate, a quartz plate, a polymer film, or the like. Depending on the application, a substrate having high transparency to ultraviolet light may be used. Examples of the polymer film having high transmittance to visible light include polymer films for various optical films used as members of display devices such as liquid crystal display devices. Examples of the substrate include a polyester film such as polyethylene terephthalate (PET), polybutylene terephthalate, and polyethylene naphthalate (PEN); a polycarbonate (PC) film and a polymethyl methacrylate film; a polyolefin film such as polyethylene and polypropylene; and a polyimide film and a triacetyl cellulose (TAC) film. A polyethylene terephthalate film and a triacetyl cellulose film are preferable.

[Alignment Layer]

The film may have an alignment layer between the substrate and the cured film. The alignment layer has a function of more precisely defining the alignment direction of the liquid crystal compound. The alignment layer can be provided by means such as a rubbing treatment of an organic compound (preferably, a polymer), oblique vapor deposition of an inorganic compound, and formation of a layer having microgrooves. There is also known an alignment layer in which an orientation function is generated by application of an electric field, application of a magnetic field, or photoirradiation. It is preferable that the alignment layer is formed by performing a rubbing treatment on the surface of the polymer film.

As the material used in the alignment layer, a polymer of an organic compound is preferable, and a polymer which is crosslinked by itself or a polymer which is crosslinked by a crosslinking agent is frequently used. It is obvious that a polymer having both functions is also used. Examples of the polymer include polymers such as polymethyl methacrylate, an acrylic acid/methacrylic acid copolymer, a styrene/maleinimide copolymer, polyvinyl alcohol and modified polyvinyl alcohol, poly(N-methylolacrylamide), a styrene/vinyltoluene copolymer, chlorosulfonated polyethylene, nitrocellulose, polyvinyl chloride, chlorinated polyolefin, polyester, polyimide, a vinyl acetate/vinyl chloride copolymer, an ethylene/vinyl acetate copolymer, carboxymethyl cellulose, gelatin, polyethylene, polypropylene, and polycarbonate, and a compound such as a silane coupling agent. Examples of preferred polymers include a water-soluble polymer such as poly(N-methylolacrylamide), carboxymethyl cellulose, gelatin, polyvinyl alcohol, and modified polyvinyl alcohol. Among these, gelatin, polyvinyl alcohol, and modified polyvinyl alcohol are preferable, and polyvinyl alcohol and modified polyvinyl alcohol are particularly preferable.

[Adhesive Layer]

In a case where a plurality of cured films are bonded to each other with an adhesive, an adhesive layer is provided between the cured films. The adhesive layer may be formed of an adhesive agent.

In view of a curing method, examples of the adhesive include a hot melt type, a thermosetting type, a photocuring type, a reaction curing type, and a pressure-sensitive adhesive type unnecessary for curing. As the materials, acrylate-based, urethane-based, urethane acrylate-based, epoxy-based, epoxy acrylate-based, polyolefin-based, modified olefin-based, polypropylene-based, ethylene vinyl alcohol-based, vinyl chloride-based, chloroprene rubber-based, cyanoacrylate-based, polyamide-based, polyimide-based, polystyrene-based, and polyvinyl butyral-based compounds, and the like can be used. In view of workability and productivity, a photocuring type is preferable as a curing method. In view of optical transparency and heat resistance, as the material, acrylate-based, urethane acrylate-based, epoxy acrylate-based compounds are preferably used.

The thickness of the adhesive layer may be 0.5 to 10 μm and preferably 1 to 5 μm. In a case where the film is used as a half mirror for a projection image display, it is preferable that the adhesive layer is provided to have a uniform film thickness in order to reduce color unevenness or the like.

[Application of Film]

Examples the film formed by using the polymerizable composition include a film in which the alignment of the liquid crystalline phase (for example, horizontal alignment, vertical alignment, and hybrid alignment) of the polymerizable composition is fixed. This film generally exhibits optical anisotropy and is used as an optical compensation film for a liquid crystal display device and the like.

Other examples thereof include a film including a layer in which the cholesteric liquid crystalline phase of the polymerizable composition is fixed and which exhibits selective reflection characteristics with respect to light in a predetermined wavelength range.

In the cholesteric liquid crystalline phase, liquid crystal molecules are arranged in a helical pattern. A layer in which the cholesteric liquid crystalline phase is fixed (hereinafter, also referred to as a "cholesteric liquid crystal layer") selectively reflects any one of right-handed circular polarization and left-handed circular polarization in the selective reflection wavelength range and functions as a circular polarization selective reflection layer that transmits circular polarization of the other sense. A film containing one or more cholesteric liquid crystal layers can be used for various purposes. In a film including two or more cholesteric liquid crystal layers, the sense of circular polarization reflected by each cholesteric liquid crystal layer may be the same or reverse depending on the application. The central wavelength of selective reflection of each cholesteric liquid crystal layer described below may be identical to or different from each other according to the application.

In the present specification, the expression "sense" for circular polarization means right-handed circular polarization and left-handed circular polarization. With respect to the sense of the circular polarization light, in a case where light proceeds forward, a case where a tip of an electric field vector rotates in a clockwise direction according to the time elapse is defined as right circular polarization light, and a case where a tip of an electric field vector rotates in a counterclockwise direction is defined as left circular polarization light. In the present specification, the expression "sense" may be used for the twisted direction of the helix of the cholesteric liquid crystal. In a case where the twisted direction (sense) of the helix of the cholesteric liquid crystal is right, right-handed circular polarization is reflected and left-handed circular polarization is transmitted. In a case where the sense is left, left-handed circular polarization is reflected and right-handed circular polarization is transmitted.

For example, a film including a cholesteric liquid crystal layer exhibiting selective reflection characteristics in the visible light wavelength range (wavelength 400 to 750 nm) can be used as a screen or a half mirror for projection image display. The film can be used as a filter that improves color purity of display light of a color filter or a display (for example, see JP2003-294948A) by controlling the reflection band.

The optical film can be used for various applications such as a polarizing element, a reflection film, an antireflection film, a viewing angle compensation film, holography, and an alignment film, as a constitutional element of the optical element.

Hereinafter, the application as a member for projection image display which is a particularly preferable application is described.

[Member for Projection Image Display]

A projection image can be formed by reflecting circular polarization in any one of senses at a wavelength exhibiting selective reflection among projection light by the above function of the cholesteric liquid crystal layer. The projection image is displayed on the surface of the member for projection image display and may be visually recognized in that manner or may be a virtual image which appears to float above the member for projection image display as viewed from the observer.

A central wavelength λ of the selective reflection depends on a pitch P (=helical cycle) in a helical structure in the cholesteric phase and follows a relationship of λ=n×P with an average refractive index n of the cholesteric liquid crystal layer. Here, the central wavelength λ of the selective reflection of the cholesteric liquid crystal layer means the wavelength at the center position of the reflection peak of the circular polarization reflection spectrum measured from the normal direction of the cholesteric liquid crystal layer. As can be seen from the above equation, the central wavelength of the selective reflection can be adjusted by adjusting the pitch of the helical structure. That is, for example, in order to selectively reflect any one of the right-handed circular polarization and the left-handed circular polarization with respect to the blue light by adjusting the n value and the P value, it is possible to adjust the central wavelength λ such that the apparent central wavelength of selective reflection is in the wavelength range of 450 nm to 495 nm. Incidentally, the apparent central wavelength of selective reflection means the wavelength at the center position of the reflection peak of the circular polarization reflection spectrum of the cholesteric liquid crystal layer measured from the observation direction in practical use (in a case of being used as a member for projection image display). The pitch in the cholesteric liquid crystalline phase depends on types of a chiral agent used together with the polymerizable liquid crystal compound or addition concentration thereof. Therefore, a desired pitch can be obtained by adjusting these. With respect to the sense of a helix or a measuring method of the pitch, methods disclosed in page 46 of "Easy Steps in Liquid Crystal Chemistry Experiment" edited by The Japanese Liquid Crystal Society, Sigma Publishing, published in 2007 and page 196 of "Liquid Crystal Handbook" Editorial Committee of Liquid Crystal Handbook, Maruzen can be used in the same manner.

With respect to a half-width $\Delta\lambda$ (nm) of the selective reflection wavelength range exhibiting the circular polarization selective reflection, $\Delta\lambda$ depends on birefringence $\Delta n$ of the liquid crystal compound and the pitch P and follows a relationship of $\Delta\lambda = \Delta n \times P$. Therefore, control of the width of the selective reflection wavelength range can be performed by adjusting $\Delta n$. That is, in the cholesteric liquid crystal layer formed from a composition containing a low birefringence polymerizable liquid crystal compound of the present invention, wavelength selectivity of selective reflection can be enhanced.

For example, $\Delta\lambda/\lambda$, which is the ratio of the half-width $\Delta\lambda$ of the selective reflection wavelength range to the central wavelength $\lambda$ of the selective reflection, can be used as an index exhibiting the wavelength selectivity of the selective reflection. $\Delta\lambda/\lambda$ of the film of the present invention, particularly a film used as a member for projection image display, is preferably 0.09 or less and more preferably 0.07 or less. More specifically, in the cholesteric liquid crystal layer in the film, it is preferable that $\Delta\lambda/\lambda$ satisfies the above condition, and with respect to the film including two or more cholesteric liquid crystal layers, it is preferable that $\Delta/\lambda/\lambda$ in each of two or more cholesteric liquid crystal layers satisfies the above condition. $\Delta\lambda$ and $\lambda$ of each layer may be identical to or different from each other.

By using the above polymerizable composition, cured films having apparent central wavelengths of selective reflection respectively in a red light wavelength range, a green light wavelength range, and a blue light wavelength range were prepared respectively and were laminated, so as to produce the member for projection image display that can display a full color projection image. Specifically, it is preferable to laminate the cured films having in which the half mirrors are in the respective ranges of 750 to 620 nm, 630 to 500 nm, and 530 to 420 nm and which have different central wavelengths of selective reflection (for example, the difference is 50 nm or greater).

The central wavelength of the selective reflection of each cured film is adjusted according to the emission wavelength range of the light source used for projection and the mode of use of the member for projection image display, so as to display clear projection images with high efficiency of light utilization. Particularly, the central wavelength of the selective reflection of each cured film is adjusted according to the emission wavelength range of the light source used for projection and the like, so as to display clear projection images with high efficiency of light utilization. Examples of the aspect of the use of the member for projection image display particularly include the incidence angle of the projection light on the surface of the half mirror for projection image display and the projection image observation direction of the surface of the member for projection image display.

For example, by configuring the member for projection image display so as to have transmittance to light in the visible light region, the half mirror that can be used as a combiner of the head up display can be formed. The half-mirror for projection image display can display the image projected from a projector or the like in a viewable manner, and in a case where the half-mirror for projection image display is observed, it is possible to simultaneously observe information or landscape on the face side from the same face side on which the image is displayed.

In a case where the film is used as a half-mirror for projection image display, it is preferable to provide a cured film produced as described above, particularly, a laminate of three or more cured films on the surface of the base material. It is preferable that the base material is transparent in the visible light region and has low birefringence. For example, the retardation of the base material at the wavelength of 550 nm is preferably 50 nm or less and more preferably 20 nm or less.

Examples of the base material include inorganic glass and a polymer resin (an acrylic resin (acrylic acid esters such as polymethyl (meth)acrylate), polycarbonate, cyclic polyolefin such as cyclopentadiene-based polyolefin and norbornene-based polyolefin, polyolefins such as polypropylene, aromatic vinyl polymers such as polystyrene, polyarylate, cellulose acylate, and the like). Among these, in view of low birefringence, inorganic glass, an acrylic resin, cyclic polyolefin, polyolefins, and cellulose acylate are preferable, and inorganic glass and an acrylic resin are more preferable.

The half-mirror for projection image display may have an antireflection layer. The antireflection layer is preferably included in the outermost surface. In a case of using the half-mirror for projection image display, the antireflection layer may be provided on an outermost surface that becomes a viewing side, or may be provided on the outermost surface on the opposite side. However, it is preferable that the antireflection layer is provided on the outermost surface on the viewing side. In a case where the cured film is provided on the base material surface, an antireflection layer may be provided on both the base material side surface and the cured film side which becomes the viewing side. With such a configuration, it is difficult to generate a double image that may occur particularly in a case where the birefringence of the base material is high.

In addition to a film on which fine surface unevenness is formed, examples of the antireflection layer include films having a configuration of a two-layer film obtained by combining a layer of a high refractive index and a layer of a low refractive index and a configuration of a three-layer film obtained by sequentially laminating a layer of a medium refractive index, a layer of a high refractive index, and a layer of a low refractive index.

Examples of the configuration example include a film in which two layers of a layer of a high refractive index and a layer of a low refractive index in an order from the lower side, or a film in which three layers having different refractive indexes are laminated, in order of a layer of a medium refractive index (a layer having a higher refractive index than the underlayer and a lower refractive index than the layer of a high refractive index), a layer of a high refractive index, and a layer of a low refractive index. It is also suggested to laminate more antireflection layers. Among these, in view of durability, optical characteristics, cost, productivity, and the like, it is preferable to include a layer of a medium refractive index, a layer of a high refractive index, and a layer of a low refractive index in this order on the hard coat layer, and examples thereof include configurations disclosed in JP1996-122504A (JP-H08-122504A), JP1996-110401A (JP-H08-110401A), JP1998-300902A (JP-H10-300902A), JP2002-243906A, and JP2000-111706A. An antireflection film having a three-layer configuration excellent in robustness against film thickness fluctuation is disclosed in JP2008-262187A. The antireflection film having a three-layer configuration is provided on the surface of the image display device, the average value of the reflectivity may be caused to be 0.5% or less, and the reflected glare can be remarkably reduced. Therefore, an image having an excellent stereoscopic effect can be obtained. It is possible to impart other functions to each layer, and examples thereof include an antifouling layer of a low refractive index, an antistatic layer of a high refractive index, an antistatic hard coat layer, and an antiglare hard coat layer (for example, JP1998-206603A (JP-H10-206603A), JP2002-243906A, and JP2007-264113A).

Examples of the inorganic material forming the antireflection layer include $SiO_2$, $SiO$, $ZrO_2$, $TiO_2$, $TiO$, $Ti_2O_3$, $Ti_2O_6$, $Al_2O_3$, $Ta_2O_5$, $CeO_2$, $MgO$, $Y_2O_3$, $SnO_2$, $MgF_2$, and $WO_3$, and these may be used singly or two or more kinds thereof may be used in combination. Among these, $SiO_2$, $ZrO_2$, $TiO_2$, and $Ta_2O_5$ are preferable, since vacuum deposition is possible at low temperature and it is possible to form films also on the surface of a plastic substrate.

As a multilayer film formed of an inorganic material, a lamination structure in which a total optical thickness of the $ZrO_2$ layer and the $SiO_2$ layer from the substrate side is $\lambda/4$, an optical thickness of the $ZrO_2$ layer is $\lambda/4$, an optical thickness of the $SiO_2$ layer of the outermost layer is $\lambda/4$, and the layers of a high refractive index and the layers of a low refractive index are alternately formed is exemplified. Here, $\lambda$ is the design wavelength, 520 nm is usually used. The outermost layer is preferably formed of $SiO_2$ in which a refractive index is low and mechanical strength can be imparted to the antireflection layer.

In a case where an antireflection layer is formed of an inorganic material, as a film formation method, for example, a vacuum deposition method, an ion plating method, a sputtering method, a CVD method, and a method of precipitating by chemical reaction in a saturated solution, or the like can be employed.

Examples of the organic material used for the layer of the low refractive index include a tetrafluoroethylene-hexafluoropropylene copolymer (FFP), polytetrafluoroethylene (PTFE), and an ethylene-tetrafluoroethylene copolymer (ETFE). A composition containing a fluorine-containing curable resin and inorganic fine particles disclosed in JP2007-298974A and a hollow silica fine particle-containing coating composition of a low refractive index disclosed in JP2002-317152A, JP2003-202406A, and JP2003-292831A are suitably used. As a film formation method, in addition to the vacuum deposition method, a film can be formed by a coating method excellent in mass productivity such as a spin coating method, a dip coating method, and a gravure coating method.

The refractive index of the layer of a low refractive index is preferably 1.30 to 1.51, more preferably 1.30 to 1.46, and even more preferably 1.32 to 1.38.

Examples of the organic materials used in the layer of a medium refractive index and the layer of a high refractive index include a binder obtained by crosslinking or polymerization reaction such as an ionizing radiation curable compound containing an aromatic ring, a ionizing radiation curable compound including a halogenated element other than fluorine (for example, Br, I, and Cl), and an ionizing radiation curable compound containing atoms such as S, N, and P, and inorganic particles containing $TiO_2$ as a main component to be added thereto. Specifically, organic materials disclosed in paragraph numbers [0074] to [0094] of JP2008-262187A can be exemplified.

The refractive index of the layer of a high refractive index is preferably 1.65 to 2.20 and more preferably 1.70 to 1.80. The refractive index of the layer of a medium refractive index is adjusted so as to be a value between the refractive index of the layer of a low refractive index and the refractive index of the layer of a high refractive index. The refractive index of the layer of a medium refractive index is preferably 1.55 to 1.65 and more preferably 1.58 to 1.63.

The film thickness of the antireflection layer is not particularly limited, but may be 0.1 to 10 μm, 1 to 5 μm, and about 2 to 4 μm.

EXAMPLES

Hereinafter, characteristics of the present invention are more specifically described with reference to the examples and comparative examples. A material, an amount used, a treatment detail, a treatment order, and the like provided in the following examples can be suitably changed without departing from the gist of the present invention. The scope of the present invention should not be construed in a limited manner by the following specific examples.

In the examples, HPLC means high performance liquid chromatography, and NMR means a nuclear magnetic resonance.

<Synthesis of Compound I>

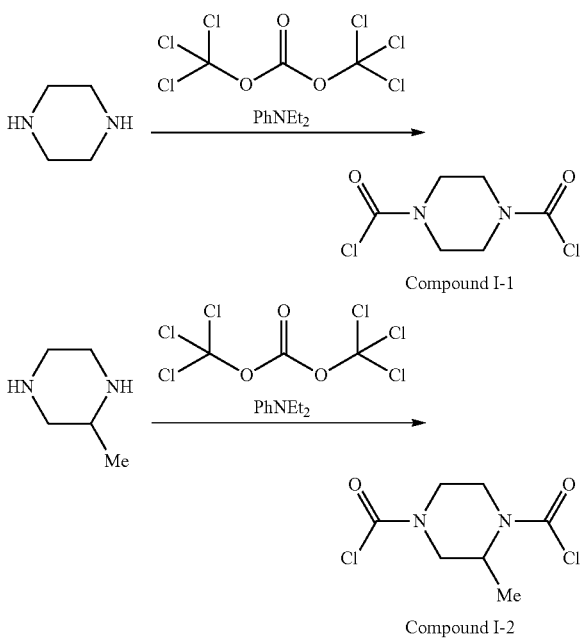

Triphosgene (12.06 g) was stirred in tetrahydrofuran (THF) (40 mL) at 0° C. and a solution obtained by mixing piperazine (5 g), N,N-diethylaniline (20.5 mL) and THF (20 mL) was added dropwise over 30 minutes, and stirring was performed at room temperature for two hours. Ethyl acetate (60 mL) and 1 N aqueous hydrochloric acid (128 mL) were added at 0° C., then the aqueous layer was removed, and the organic layer was washed with saline. The organic layer was dried over sodium sulfate, the desiccant was filtered off, and the solvent was distilled off under reduced pressure. The obtained solid was washed with hexane and filtered so as to obtain Compound I-1. Compound I-2 was obtained in the same manner.

<Synthesis of Compound II>

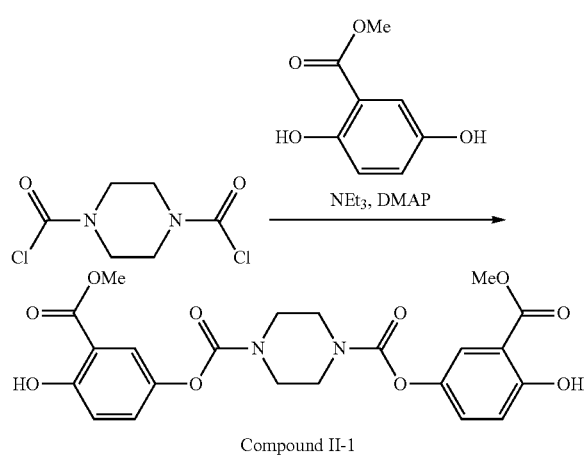

Compound II-1

Compound I-1 (3.14 g) and methyl 2,5-dihydroxybenzoate (5 g) were stirred at 0° C. in THF (20 mL), N,N-dimethyl-4-aminopyridine (DMAP, 0.18 g) was added thereto, and triethylamine (4.6 mL) was added dropwise. After stirring at room temperature for two hours, methanol was added to precipitate a solid. The obtained solid was dissolved in THF, and then methanol was added thereto so as to perform recrystallization to obtain Compound II-1.

$^1$H-NMR (solvent: CDCl$_3$) δ (ppm): 3.6-3.8 (m, 8H), 4.0 (s, 6H), 7.0 (d, 2H), 7.2 (dd, 2H), 7.6 (d, 2H), 10.6 (s, 2H)

Compound II-2 was synthesized in the same manner.

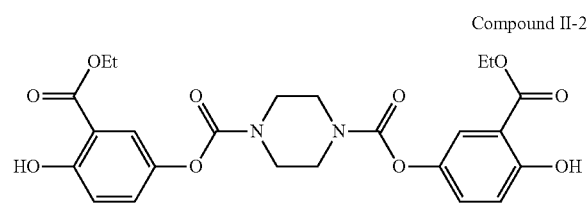 [SMILES: CCOC(=O)c1cc(OC(=O)N2CCN(C(=O)Oc3ccc(O)c(C(=O)OCC)c3)CC2)ccc1O]

Compound II-2

$^1$H-NMR (solvent: CDCl$_3$) δ (ppm): 1.4 (t, 6H), 3.6-3.8 (m, 8H), 4.4 (q, 4H), 7.0 (d, 2H), 7.2 (dd, 2H), 7.6 (d, 2H), 10.7 (s, 2H)

Compound II-3 was synthesized in the same manner.

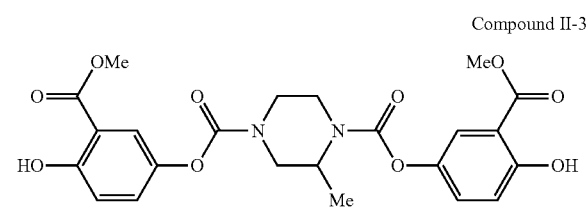 [SMILES: COC(=O)c1cc(OC(=O)N2CCN(C(=O)Oc3ccc(O)c(C(=O)OC)c3)C(C)C2)ccc1O]

Compound II-3

$^1$H-NMR (solvent: CDCl$_3$) δ (ppm): 1.4 (m, 3H), 3.1-3.4 (m, 3H), 4.0 (s, 6H), 4.0-4.3 (m, 3H), 4.5 (m, 1H), 7.0 (d, 2H), 7.2 (dd, 2H), 7.6 (d, 2H), 10.6 (s, 2H)

Compound II-4 was synthesized in the same manner.

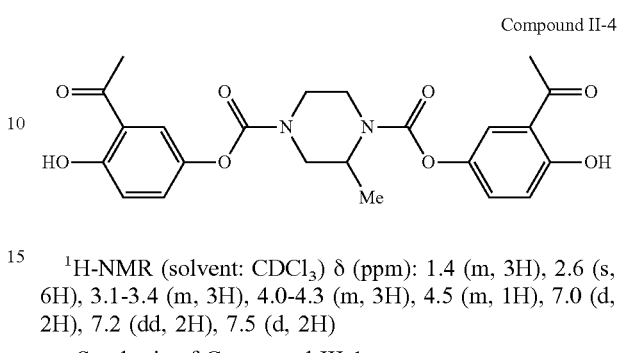

Compound II-4

$^1$H-NMR (solvent: CDCl$_3$) δ (ppm): 1.4 (m, 3H), 2.6 (s, 6H), 3.1-3.4 (m, 3H), 4.0-4.3 (m, 3H), 4.5 (m, 1H), 7.0 (d, 2H), 7.2 (dd, 2H), 7.5 (d, 2H)

<Synthesis of Compound III-1>

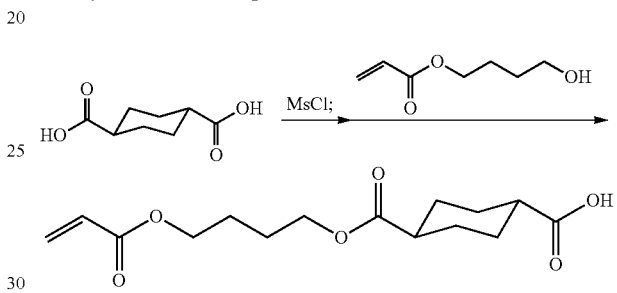

Trans-1,4-cyclohexadicarboxylic acid (10 g), mesyl chloride (1.9 mL), and dibutylhydroxytoluene (BHT: 0.2 g) were stirred in THF (72 mL), the internal temperature was maintained at 25° C. or lower, and triethylamine (3.7 mL) was added dropwise. After stirring at room temperature for two hours, N,N-dimethylaminopyridine (0.3 g) and 4-hydroxybutyl acrylate (3.1 g) were added, and triethylamine (3.7 mL) was added dropwise at an internal temperature of 25° C. or lower. After stirring at room temperature for three hours, diluted hydrochloric acid and ethyl acetate were added to remove the aqueous layer, and washing with diluted hydrochloric acid, saturated sodium bicarbonate water, and saline in this order was performed. The organic layer was dried over magnesium sulfate, the desiccant was filtered off, and the solvent was distilled off under reduced pressure to obtain carboxylic acid III-1 (7.1 g).

$^1$H-NMR (Solvent: CDCl$_3$) δ (ppm):

1.4-1.6 (m, 4H), 1.6-1.8 (m, 4H), 2.0-2.2 (m, 4H), 2.2-2.4 (m, 2H), 4.1 (t, 2H), 4.2 (t, 2H), 5.8 (dd, 1H), 6.1 (dd, 1H), 6.4 (dd, 1H)

<Synthesis of Compound 1>

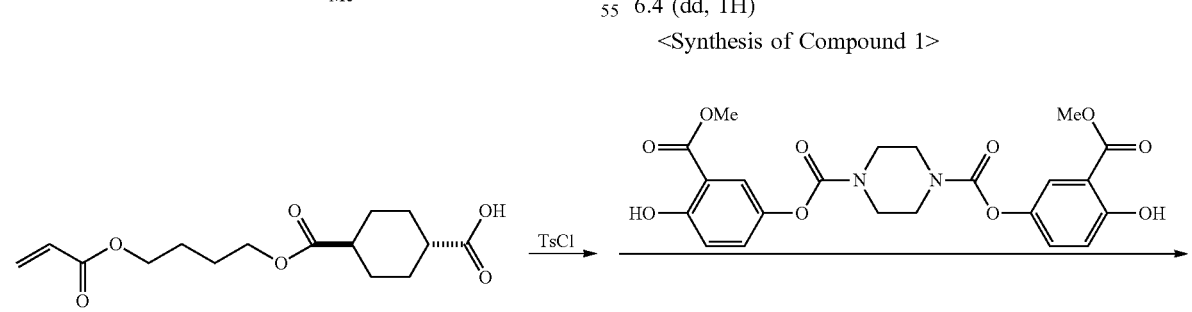

-continued

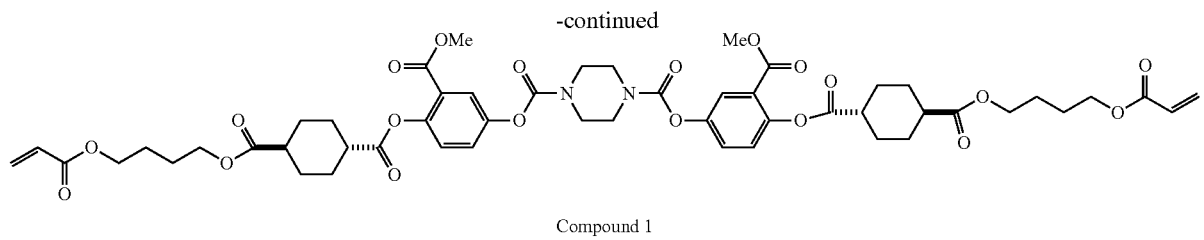

Compound 1

Carboxylic acid III-1 (1.57 g), TsCl (1.21 g) and BHT (0.02 g) were stirred in THF (5 mL) and 1-ethyl 2-pyrrolidone (3 mL), 1-methyl imidazole (1.26 mL) was added dropwise under ice cooling, and stirring was performed at room temperature for one hour. Compound II-1 (1.0 g) was added and stirring was further performed at room temperature for two hours. After water (10 mL) was added, the aqueous layer was removed, water and methanol were added, stirring was performed for one hour under ice cooling, and the generated crystals were filtered to obtain Compound 1 (0.85 g).

$^1$H-NMR (solvent: CDCl$_3$) δ (ppm): 1.4-1.7 (m, 8H), 1.7-1.8 (m, 8H), 2.1-2.2 (m, 4H), 2.2-2.4 (m, 6H), 2.6 (m, 2H), 3.6-3.8 (m, 8H), 3.8 (s, 6H), 4.1-4.3 (m, 8H), 5.8 (d, 2H), 6.1 (dd, 2H), 6.4 (d, 2H), 7.1 (d, 2H), 7.3 (dd, 2H), 7.8 (d, 2H)

Compound 3 was synthesized in the same manner by using Compound II-3 instead of Compound II-1.

Compound 3

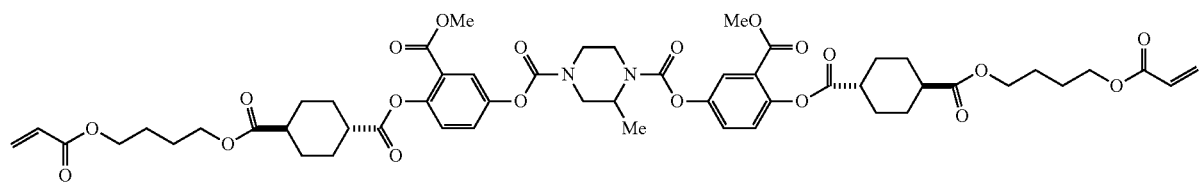

$^1$H-NMR (solvent: CDCl$_3$) δ (ppm): 1.4 (m, 3H), 1.4-1.7 (m, 8H), 1.7-1.8 (m, 8H), 2.1-2.2 (m, 4H), 2.2-2.4 (m, 6H), 2.6 (m, 2H), 3.1-3.4 (m, 3H), 3.8 (s, 6H), 4.1-4.3 (m, 11H), 4.5 (m, 1H), 5.8 (d, 2H), 6.1 (dd, 2H), 6.4 (d, 2H), 7.1 (d, 2H), 7.3 (dd, 2H), 7.8 (d, 2H)

<Synthesis of Compound 2>

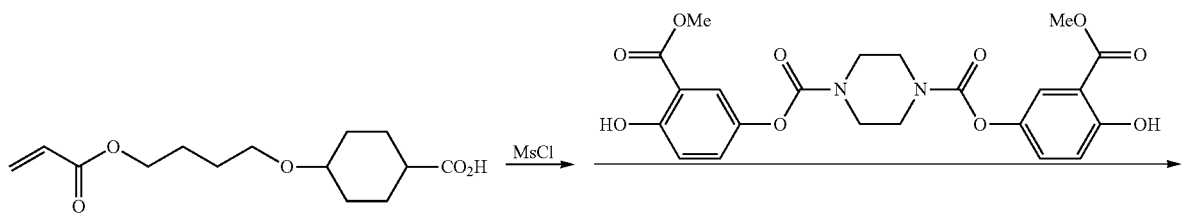

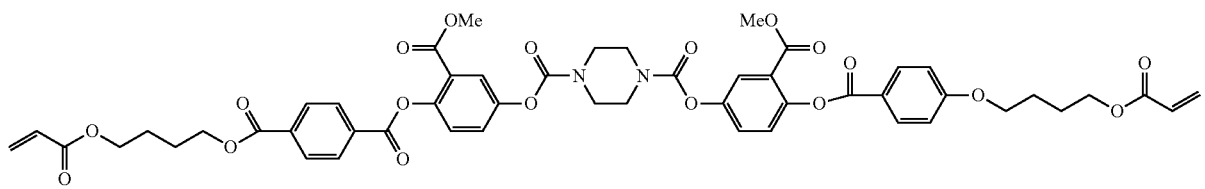

Compound 2

4-(4-acryloyloxybutyloxy) benzoic acid was synthesized by referring to the method disclosed in paragraph [0085] to [0087] of page 18 of JP4397550B.

BHT (0.01 g) was added to a solution of methanesulfonyl chloride (0.57 g), tetrahydrofuran (1 mL) and ethyl acetate (4 mL), and the internal temperature was cooled to −5° C. A separately prepared solution of 4-(4-acryloyloxybutyloxy) benzoic acid (1.28 g) and triethylamine (0.53 g) in tetrahydrofuran (3 mL) was added dropwise such that the internal temperature did not rise above 0° C. After stirring was performed at −5° C. for one hour, a small amount of N-methylimidazole was added, the compound II-1 (1 g) was added, 3.5 mL of tetrahydrofuran was added, triethylamine (0.53 g) was added dropwise, and stirring was performed for two hours at room temperature. Water (4 mL) was added to stop the reaction, ethyl acetate was added to remove the aqueous layer, and washing was performed with the diluted hydrochloric acid and saline in this order. After a desiccant was added and filtration was performed, methanol (10 mL) was added thereto, and the resulting crystals were filtered to obtain 1.6 g of a compound 2.

$^1$H-NMR (solvent: CDCl$_3$) δ (ppm): 1.9-2.0 (m, 8H), 3.7-3.8 (m, 8H), 3.7 (s, 6H), 4.1 (m, 4H), 4.3 (m, 4H), 5.8 (d, 2H), 6.1 (dd, 2H), 6.4 (d, 2H), 7.0 (d, 4H), 7.2 (d, 2H), 7.4 (dd, 2H), 7.8 (d, 2H), 8.2 (d, 4H)

Compound 4 was synthesized in the same manner by using Compound II-3 instead of Compound II-1.

Compound 4

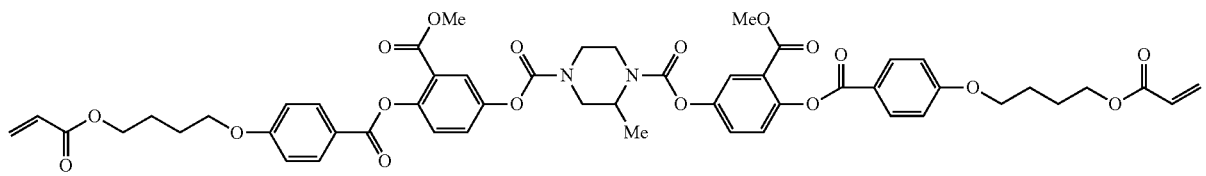

$^1$H-NMR (solvent: CDCl$_3$) δ (ppm): 1.1 (t, 6H), 1.9-2.0 (m, 8H), 3.7-3.8 (m, 8H), 4.1 (m, 4H), 4.2 (q, 4H), 4.3 (m, 4H), 5.8 (d, 2H), 6.1 (dd, 2H), 6.4 (d, 2H), 7.0 (d, 4H), 7.2 (d, 2H), 7.4 (dd, 2H), 7.8 (d, 2H), 8.2 (d, 4H)

Compound 5 was synthesized in the same manner by using Compound II-2 instead of Compound II-1.

Compound 5

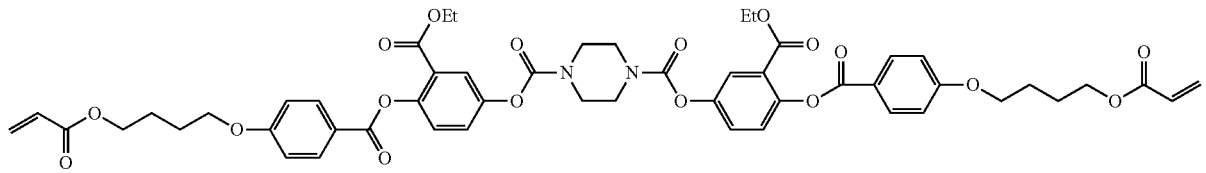

$^1$H-NMR (solvent: CDCl$_3$) δ (ppm): 1.4 (m, 3H), 1.9-2.0 (m, 8H), 3.1-3.5 (m, 3H), 3.7 (s, 6H), 4.1-4.3 (m, 11H), 4.6 (m, 1H), 5.8 (d, 2H), 6.1 (dd, 2H), 6.4 (d, 2H), 7.0 (d, 4H), 7.2 (d, 2H), 7.4 (dd, 2H), 7.8 (d, 2H), 8.2 (d, 4H)

Compound 6 was synthesized in the same manner by using Compound II-4 instead of Compound II-1.

Compound 6

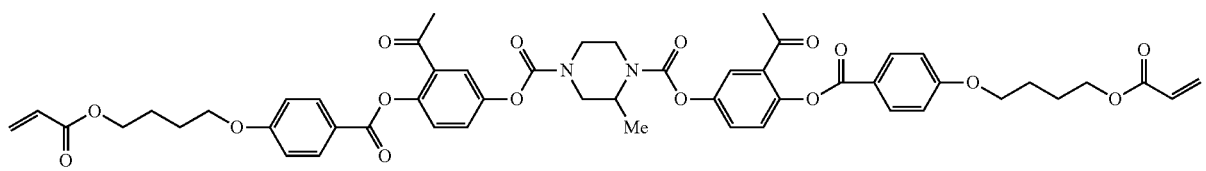

$^1$H-NMR (solvent: CDCl$_3$) δ (ppm): 1.4 (m, 3H), 1.9-2.0 (m, 8H), 2.5 (s, 6H), 3.1-3.5 (m, 3H), 4.1-4.4 (m, 11H), 4.6 (m, 1H), 5.8 (d, 2H), 6.1 (dd, 2H), 6.4 (d, 2H), 7.0 (d, 4H), 7.2 (d, 2H), 7.4 (dd, 2H), 7.6 (d, 2H), 8.2 (d, 4H)

Reference Example 1

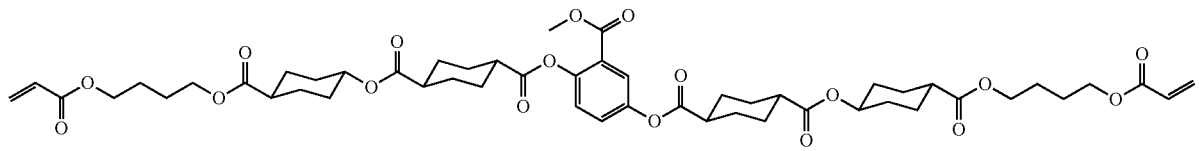

Compound 7

Comparative Example 1 (Compound Disclosed in JP5082538B)

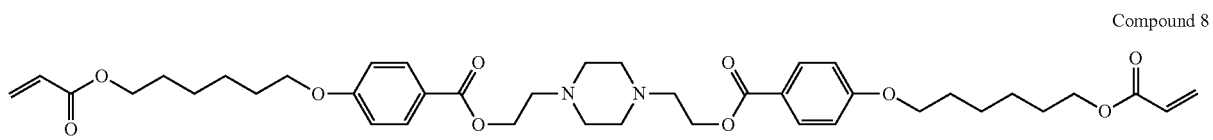

Compound 8

<Evaluation of Compounds>

Each of the compounds was evaluated in the following standards.

[Liquid Crystallinity]

The phase transition temperature was measured by observing each compound with a polarization microscope while heating and cooling.

[Measurement of Birefringence]

The birefringence (Δn) of each compound and a well-known compound in the related art was measured by a method disclosed in p. 202 of Liquid Crystal Handbook (Liquid Crystal Handbook Editing Committee). Specifically, a sample was injected into a wedge-shaped cell, the sample was irradiated with a laser beam having a wavelength of 550 nm, and the refraction angle of transmitted light was measured, so as to obtain Δn in an NI point of each compound or composition −60° C. (an NI point is a nematic-isotropic phase transition point). With respect to Compounds 1, 3, and 7, Δn was measured as a composition (33 wt %) with M-1.

[Stability (Decomposition Rate)]

26 mg of each compound was dissolved in 1 ml of a solvent of acetonitrile:water=1:1 (volume fraction), and the difference in area % of HPLC data around 90° C. for 24 hours was calculated as a decomposition rate.

[Coloration]

Each compound was left to stand as a powder under a condition of a temperature of 85° C. and a humidity of 85% for 24 hours, and the presence or absence of coloration was visually evaluated.

No coloration: A
Coloration: B

TABLE 1

| | Compound | Liquid crystallinity (phase transition) | Stability (decomposition rate) | Coloration (under high temperature and high humidity) |
|---|---|---|---|---|
| Example 1 | Compound 1 | Cry 135 Iso (Iso 95 Ne 92 Cry) | 3% | A |
| Example 2 | Compound 2 | Cry 105 Ne 174 Iso | 14% | A |
| Example 3 | Compound 3 | Cry 115 Iso (Iso 52 Ne 43 Cry) | 7% | A |
| Example 4 | Compound 4 | Cry 88 Ne 151 Iso | 15% | A |
| Example 5 | Compound 5 | Cry 112 Ne 138 Iso | 1% | A |
| Reference Example 1 | Compound 7 | Cry 98 Sm 103 Ne 213 Iso | 50% | A |
| Comparative Example 1 | Compound 8 | Cry 107 Iso [Uneven crystallinity] | 27% | B |
| Comparative Example 2 | M-1 | Cry 79 Ne 123 Iso | 2% | A |

| | Compound | Addition amount (parts by mass) | M-1 (parts by mass) | NI point | Δn |
|---|---|---|---|---|---|
| Example 1 | Compound 1 | 33 | 67 | 113° C. | 0.151 |
| Example 2 | Compound 2 | 100 | 0 | 174° C. | 0.14 |
| Example 3 | Compound 3 | 33 | 67 | 106° C. | 0.151 |
| Example 4 | Compound 4 | 100 | 0 | 149° C. | 0.154 |
| Example 5 | Compound 5 | 100 | 0 | 138° C. | 0.154 |
| Reference Example 1 | Compound 7 | 33 | 67 | 137° C. | 0.122 |
| Comparative Example 1 | Compound 8 | 100 | 0 | — | — |
| Comparative Example 2 | M-1 | 100 | 0 | 123° C. | 0.167 |

<Manufacturing of Retardation Film>

A liquid crystal composition coating solution (1) in the following composition was prepared by using exemplified compound synthesized in the above examples.

| | |
|---|---|
| Compound 1 | 55 parts by mass |
| Compound 2 | 30 parts by mass |
| Compound (M-1) | 15 parts by mass |
| Air interface alignment agent (1) | 0.05 parts by mass |
| Chiral agent LC-756 (manufactured by BASF SE) | 4.4 parts by mass |
| Polymerization initiator IRGACURE OXE-01 (manufactured by BASF SE) | 0.75 parts by mass |
| Solvent chloroform | 300 parts by mass |

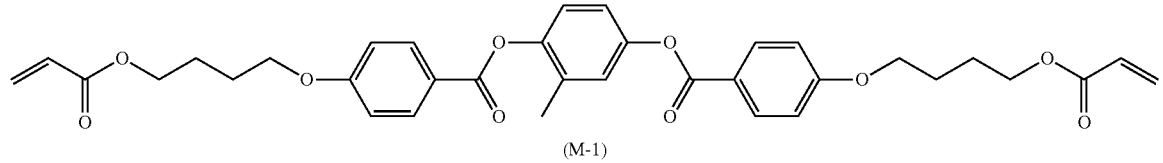

(M-1)

Subsequently, the washed glass substrate was coated with a polyimide alignment film SE-130 manufactured by Nissan Chemical Industries, Ltd. by a spin coating method, and baking was performed at 250° C. for one hour after drying. This was subjected to a rubbing treatment to manufacture a substrate with an alignment film. The rubbing-treated surface of the manufactured substrate with an alignment film was coated with the liquid crystal composition coating solution (1) at room temperature by a spin coating method, alignment ripening was performed for one minute at 90° C., photoirradiation was performed for 10 seconds using a high pressure mercury lamp at 50° C. under a nitrogen gas atmosphere, so as to fix the alignment, and a retardation film was formed.

The transmission spectrum of this film was measured with a spectrophotometer UV-3100PC manufactured by Shimadzu Corporation, there was a selective reflection peak having a center at 586 nm, and half-width thereof was 52 nm. The ratio ($\Delta\lambda/\lambda$) of the half-width of the selective reflection wavelength range to the central wavelength of selective reflection was 0.0887.

A liquid crystal composition coating solution (2) in the following composition was prepared.

| | |
|---|---|
| Compound (M-1) | 100 parts by mass |
| Chiral agent LC-756 (manufactured by BASF SE) | 5.4 parts by mass |
| Air interface alignment agent (1) | 0.1 parts by mass |
| Polymerization initiator IRGACURE819 (manufactured by BASF SE) | 3 parts by mass |
| Solvent chloroform | 300 parts by mass |

A selective reflection film (2) was manufactured in the same method as the manufacturing of the selective reflection film (1) except for using the liquid crystal composition coating solution (2) instead of the liquid crystal composition coating solution (1). At this point, after the coating solution (2) was applied until polymerization is performed, the precipitation of crystals was seen in a portion of the coated surface, such that the surface shape became uneven.

The transmission spectrum of an even portion of the selective reflection film (2) was measured, there was a selective reflection peak having a center at 569 nm, and a half-width thereof was 71 nm. The ratio ($\Delta\lambda/\lambda$) of the half-width of the selective reflection wavelength range to the central wavelength of selective reflection was 0.125.

What is claimed is:
1. A polymerizable liquid crystal compound represented by:

$$Q^1—Sp^1—[A—L]—A—Sp^2—Q^2 \qquad (I)$$

in Formula (I),

A represents a nitrogen-containing saturated cyclic group that may have a substituent, a phenylene group that may have a substituent, or a trans-1,4-cyclohexylene group that may have a substituent, wherein the nitrogen-containing saturated cyclic group is a divalent group formed by removing two hydrogen atoms from piperidine or piperazine, L represents a single bond, or a linking group selected from the group consisting of —CH$_2$O—, —OCH$_2$—, —(CH$_2$)$_2$OC(=O)—, —C(=O)O(CH$_2$)$_2$—, —C(=O)O—, —OC(=O)—, —OC(=O)O—, —CH=CH—C(=O)O—, and —OC(=O)—CH=CH—, m represents an integer of 3 to 12, Sp$^1$ and Sp$^2$ each independently represent a single bond or a linking group selected from the group consisting of a linear or branched alkylene group having 1 to 20 carbon atoms and a group in which one or more —CH$_2$—'s in a linear or branched alkylene group having 1 to 20 carbon atoms are substituted with —O—, —S—, —NH—, —N(CH$_3$)—, —C(=O)—, —OC(=O)—, or —C(=O)O—, and Q$^1$ and Q$^2$ each independently represent a hydrogen atom or a polymerizable group selected from the group consisting of groups represented by Formulae Q-1 to Q-5, here, at least one of Q$^1$ and Q$^2$ represents a polymerizable group;

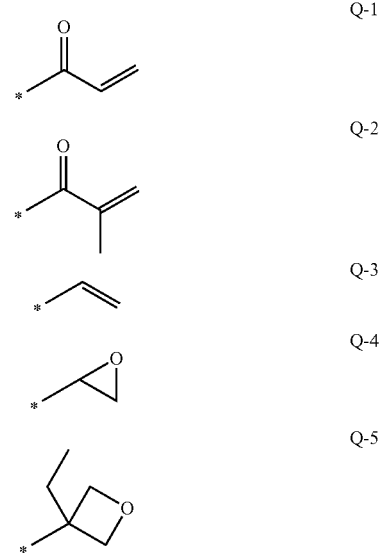

Formula (I) includes a partial structure represented by Formula (V):

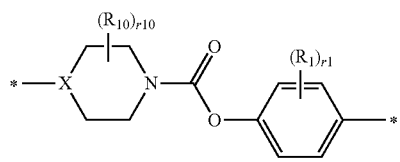

Formula (V)

in the formula, X represents N or CH, $R_1$ represents a substituent, $R_{10}$ represents a substituent, r1 and r10 each independently represent an integer of 0 to 4, a plurality of $R_1$'s in a case where r1 is 2 to 4 may be identical to or different from each other, a plurality of $R_{10}$'s in a case where r10 is 2 to 4 may be identical to or different from each other, and * represents a bonding site to another portion of Formula (I), Formula (I) includes
at least one of a phenylene group that is substituted with a group represented by —C(=O)—$X^3$—$Sp^3$—$Q^3$ or a trans-1,4-cyclohexylene group that is substituted with a group represented by —C(=O)—$X^3$—$Sp^3$—$Q^3$ as A, wherein, $X^3$ represents a single bond, —O—, —S—, or —N($Sp^4$—$Q^4$)—, or a nitrogen atom that forms a ring structure together with $Q^3$ and $Sp^3$, $Sp^3$ and $Sp^4$) each independently represent a single bond and a linking group selected from the group consisting of a linear or branched alkylene group having 1 to 20 carbon atoms and a group in which one or more —$CH_2$—'s in a linear or branched alkylene group having 1 to 20 carbon atoms are substituted with —O—, —S—, —NH—, —N($CH_3$)—, —C(=O)—, —OC(=O)—, or —C(=O)O—, and $Q^3$ and $Q^4$ each independently represent a hydrogen atom, a cycloalkyl group, a group in which one or more —$CH_2$—'s in a cycloalkyl group are substituted with —O—, —S—, —NH—, —N($CH_3$)—, —C(=O)—, —OC(=O)—, or —C(=O)O—, or any one polymerizable group selected from the group consisting of groups represented by Formulae Q-1 to Q-5,
the optional substituent on the groups that A represents is selected from the group consisting of an alkyl group, a cycloalkyl group, an alkoxy group, an alkyl ether group, an amide group, an amino group, a halogen atom, and a group obtained by combining two or more of the above substituents, or is a substituent represented by —C(=O)—$X^3$—$Sp^3$—$Q^3$, where $X^3$, $Sp^3$ and $Q^3$ have the same meanings as set forth above,
the substituent represented by $R^1$ is selected from the group consisting of an alkyl group, an alkoxy group, and —C(=O)—$X^3$—$Sp^3$—$Q^3$, where $X^3$, $Sp^3$ and $Q^3$ have the same meanings as set forth above, and
the substituent represented by $R^{10}$ is an alkyl group having 1 to 5 carbon atoms.

2. The polymerizable liquid crystal compound according to claim 1,
wherein $R_1$ is a group represented by —C(=O)—$X^3$—$Sp^3$—$Q^3$.

3. The polymerizable liquid crystal compound according to claim 2,
wherein $X^3$ is —O—, $Sp^3$ is a linear or branched alkylene group having 1 to 20 carbon atoms, and $Q^3$ is a hydrogen atom.

4. The polymerizable liquid crystal compound according to claim 1,
wherein Formula (I) includes a partial structure represented by Formula (V-1) as the partial structure (V),

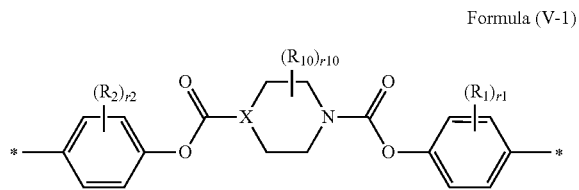

Formula (V-1)

in the formula, X represents N or CH, $R_1$ and $R_{10}$ have the same meanings as in claim 1, respectively, $R_2$ represents a substituent selected from the group consisting of an alkyl group, an alkoxy group, and —C(=O)—$X^3$—$Sp^3$—$O^3$, where $X^3$, $Sp^3$ and $Q^3$ have the same meanings as in claim 1, respectively, r1, r2, and r10 each independently represent an integer of 0 to 4, a plurality of $R_1$'s in a case where r1 is 2 to 4 may be identical to or different from each other, a plurality of $R_2$'s in a case where r2 is 2 to 4 may be identical to or different from each other, a plurality of $R_{10}$'s in a case where r10 is 2 to 4 may be identical to or different from each other, and * represents a bonding site to another portion of Formula (I).

5. The polymerizable liquid crystal compound according to claim 4,
wherein $R_1$ is a group represented by —C(=O)—$X^3$—$Sp^3$—$Q^3$.

6. The polymerizable liquid crystal compound according to claim 5,
wherein $X^3$ is —O—, $Sp^3$ is a linear or branched alkylene group having 1 to 20 carbon atoms, and $Q^3$ is a hydrogen atom.

7. The polymerizable liquid crystal compound according to claim 5,
wherein $R_2$ is a group represented by —C(=O)—$X^3$—$Sp^3$—$Q^3$.

8. The polymerizable liquid crystal compound according to claim 5,
wherein $R_1$ and $R_2$ are identical to each other and r1 and r2 are identical to each other.

9. The polymerizable liquid crystal compound according to claim 8,
wherein $R_{10}$ is a methyl group or an ethyl group.

10. The polymerizable liquid crystal compound according to claim 9,
wherein r10 represents 0 or 1.

11. The polymerizable liquid crystal compound according to claim 1,
wherein, in Formula (I), substituents that may be included in the phenylene group and the trans-1,4-cyclohexylene group are selected from the group consisting of an alkyl group having 1 to 30 carbon atoms, an alkoxy group having 1 to 30 carbon atoms, and a group represented by —C(=O)—$X^3$—$Sp^3$—$Q^3$, here, $X^3$ represents a single bond, —O—, —S—, or —N($Sp^4$—$Q^4$)—, or a nitrogen atom that forms a ring structure together with $Q^3$ and $Sp^3$, $Sp^3$ and $Sp^4$ each independently represent a single bond and a linking group selected from the group consisting of a linear or branched alkylene group having 1 to 20 carbon atoms and a group in which one or more —$CH_2$—'s in a linear or branched alkylene group having 1 to 20 carbon atoms are substituted with —O—, —S—, —NH—, —N(CH$_3$)—, —C(=O)—, —OC(=O)—, or —C(=O)O—, and Q$^3$ and Q$^4$ each independently represent a hydrogen atom, a cycloalkyl group having 3 to 20 carbon atoms, a group in which one or more —CH$_2$—'s in a cycloalkyl group are substituted with —O—, —S—, —NH—, —N(CH$_3$)—, —C(=O)—, —OC(=O)—, or —C(=O)O—, or any one polymerizable group selected from the group consisting of groups represented by Formulae Q-1 to Q-5.

12. The polymerizable liquid crystal compound according to claim 1,
wherein all of L's represent linking groups selected from the group consisting of —C(=O)O— and —OC(=O)—.

13. A polymerizable composition comprising:
the polymerizable liquid crystal compound according to claim 1.

14. The polymerizable composition according to claim 13,
wherein the polymerizable liquid crystal compound is included by 10 mass % or greater with respect to a solid content mass of the polymerizable composition.

15. The polymerizable composition according to claim 13, further comprising:
a crosslinking agent.

16. The polymerizable composition according to claim 13, further comprising:
a polymerization initiator.

17. The polymerizable composition according to claim 13, further comprising:
a chiral compound.

18. A film comprising:
a layer obtained by curing the polymerizable composition according to claim 13.

* * * * *